United States Patent [19]
Pollock et al.

[11] Patent Number: 6,027,925
[45] Date of Patent: *Feb. 22, 2000

[54] PRODUCTION OF NON-NATIVE BACTERIAL EXOPOLYSACCHARIDE IN A RECOMBINANT BACTERIAL HOST

[75] Inventors: Thomas J. Pollock, San Diego; Marcia Mikolajczak, Encinitas; Motohide Yamazaki, San Diego; Linda Thorne, Palomar; Richard W. Armentrout, La Jolla, all of Calif.

[73] Assignees: Shin-Etsu Bio, Inc., San Diego, Calif.; Shin-Etsu Chemical Co., Ltd., Tokyo, Japan

[ * ] Notice: This patent is subject to a terminal disclaimer.

[21] Appl. No.: 09/096,942

[22] Filed: Jun. 12, 1998

Related U.S. Application Data

[63] Continuation-in-part of application No. 09/096,867, Jun. 11, 1998.
[60] Provisional application No. 60/049,428, Jun. 12, 1997.
[51] Int. Cl.[7] .............................. C12P 19/06; C12P 19/04; C12N 1/20; C12N 5/00; C07H 21/04
[52] U.S. Cl. ........................ 435/104; 435/101; 435/252.3; 435/471; 435/320.1; 435/910; 536/23.2
[58] Field of Search ..................................... 435/101, 104, 435/252.3, 320.1, 471, 910; 536/23.2

[56] References Cited

PUBLICATIONS

Pollock et al. (1994) Mechanism of Bacitracin Resistance in Gram–Negative Bacteria That Synthesize Exopolysaccharides. J. Bacteriol. 176 (20): 6229–6237.

Yamazaki et al. (1996) Linkage of Genes Essential for Synthesis of a Polysaccharide Capsule in Sphingomonas Strain S88. J. Bacteriol. 178 (9): 2676–2687.

Papoutsopolou (1994) Genetic Construction of Xanthomonas campestris and Xanthan Gum Production From Whey. Biotechnol. Letts. 16 (12): 1235–1240.

*Primary Examiner*—Lisa J. Hobbs
*Attorney, Agent, or Firm*—McAulay Nissen Goldberg Kiel & Hand, LLP

[57] ABSTRACT

A recombinant bacteria for the production of exopolysaccharides is disclosed as well as a method for making the recombinant bacteria and making an exopolysaccharide from the bacteria by submerged aerobic fermentation of the bacteria utilizing a sugar substrate. In addition, the present invention provides a method of producing bacterial exopolysaccharides by fermentation from sugar substrates that the wild-type bacteria for producing the exopolysaccharide cannot utilize.

21 Claims, 2 Drawing Sheets

Xanthan gum

Sphingan S-88

X. campestris gum gene cluster

Sphingomonas S88 sps gene

SEQUENCE LISTING

<160> NUMBER OF SEQ ID NOS: 2

<210> SEQ ID NO 1
<211> LENGTH: 16075
<212> TYPE: DNA
<213> ORGANISM: Xanthomonas campestris
<300> PUBLICATION INFORMATION:

<400> SEQUENCE: 1
ggatccggtt gaggcggtaa caggggattg gcatggcatt gacgaaagcg gagatggccg 60
agcgtctgtt cgacgaagtc ggcctgaaca agcgtgaggc gaaggaattc gtcgacgcgt 120
ttttcgatgt gctgcgcgat gcactggagc agggccgtca ggtgaagttg tcgggcttcg 180
gcaacttcga tctgcggcgc aagaaccaac ggcccggtcg caatcccaag accggtgagg 240
aaattccgat ctcggccagg acggtggtga ccttccgccc cggccagaaa ctcaaggaac 300
gggtggaggc ttatgctgga tccgggcagt aatcgcgagc taccgccgat tccggccaag 360
cgctacttca ccatcggtga ggtgagcgag ctgtgcgacg tcaagccgca cgtgctgcgc 420
tattgggaaa ccgaatttcc gagcctggag gccagtcaag cggcgcgcaa ccgacgctac 480
taccagcggc acgatgtcgt gatggtgcgg cagattcgtg gcctgctgta cgagcagggt 540
tacaccatcg gggcgcgcg tctgcgtctt gaaggggatg gggccaagag cgagtcagcg 600
ctgagcaatc agatcatcaa gcaggtgcgc atggagcttg aagaagtcct gcagctgctg 660
cgacgctagg aaagcgccgc ataaagccgc tataatcgca ggccgcctca gggcgggacg 720
caacatcttc ggggtatagc gcagcctggt agcgcactag tctgggggac tagtggtcgt 780
cggttcgaat ccggctaccc cgaccaaaca acaggcctac gtcgcaagac gtgggccttt 840
ttgttgcgtc gcaacatgtc agttcgatgg cattccaggc tatgccacta tgcgcaacgg 900
catattgcaa ggcggcatat gcaagtcctg tacgcaatta tttcgcggtt caggctgcta 960
caagtcggga tcagcaggcg tccgtaagtg cccggaaacg ctagagttcg tatgctgaga 1020
atgacgaccc aggtcacgtt ctcttaacgt cgaggcgacg aacttgaatc aataggccaa 1080
cgccgtcaaa aaaatggcgt gttgtgcctt gcgatgtgtt cgttctatgc catagtgcac 1140
tgcaacacgc gattcaacgt tggtcccggc acgcgtcggg atgcaacttc ctgtcgtacg 1200
ttcgtgctgg cgcctgagcc ggttgaatgc tgcgcgaggt cctgtcccac ccaacagagg 1260
cagccagcta cacgcatgaa gaaactgatc ggacgactcg tcgcaaggcc tcagcctggc 1320
tctgctctgc tcgatgtcgc tgggcgcttg cagcaccggc ccggagatgg cgtcttcgct 1380
gccgcatccg gacccgctgg caatgtccac ggtgcagccc gaataccgtc ttgcgccggg 1440
cgatctgttg ctggtgaagg tgtttcagat cgacgatctg gagcggcagg tccgcatcga 1500
ccagaacggt cacatctcac tgccgttgat tggcgacgtc aaggccgccg gtctgggcgt 1560
tggcgaactg gaaaagctgg tcgccgatcg gtatcgcgca ggctacctgc agcagccgca 1620
gatttcggta ttcgtgcagg agtccaacgg gcgtcgcgtc acggtcactg gtgcggtaga 1680
cgagccgggc atctacccgg tgatcggcgc caacctcacc ttgcagcagg cgatcgcgca 1740
ggccaagggt gtcagcacgg tggcaagccg cggcaacgtg atcgtgttcc gcatggtcaa 1800
cgggcaaaaa atgattgcgc ggttcgacct gaccgagatc gagaaggggg ccaatccgga 1860
tcctgagatt tatggcggcg acattgtcgt ggtgtatcgc tcggatgcgc gcgtgtggtt 1920
gcgcaccatg ctggaactga ccccttggt gatggtgtgg cgcgcttacc gatgagtatg 1980

-continued

```
aattcagaca atcgttcctc ttcgtcgcag cggtcatggt catctggaac tggcagatgt    2040
cgacttgatg gactactggc gcgccctggt ctcgcagctc tggctgatca tcctgatcgc    2100
cgtcggcgcg ctgttgctgg cattcggcat cacgatgttg atgcccgaga agtaccgcgc    2160
caccagcacc ctgcagatcg aacgtgactc gctcaatgtg gtgaacgtcg acaacctgat    2220
gccggtggaa tcgccgcagg atcgcgattt ctaccagacc cagtaccagt tgctgcagag    2280
ccgttcgctg gcgcgtgcgg tgatccggga agccaagctc gatcaggagc cggcgttcaa    2340
ggagcaggtg gaggaggcgc tggccaaagc cgccgaaaag aatcccgagg cgggtaagtc    2400
gctcgattcg cggcaggcga tcgtcgagcg cagcctcacc gatacgttgc tcgccgggct    2460
ggtggtcgag ccgatcctca actcgcgcct ggtgtacgtc aattacgatt cgccagaccc    2520
ggtgctggcc gccaagatcg ccaatacgta cccgaaggtg ttcatcgtca gcacccagga    2580
acgccgcatg aaggcgtctt cgtttgcgac acagtttctg gctgagcgcc tgaagcagtt    2640
gcgcgagaag gtcgaagact ctgaaaagga tctggtctcg tattcgaccg aagagcagat    2700
cgtgtcggtt ggcgatgaca agccctcgct gcctgcgcag aatctgaccg atctcaatgc    2760
gttgctggca tccgcacagg acgcccggat caaggccgag tcagcttggc ggcaggcttc    2820
cagtggcgat ggcatgtcat tgccgcaggt gttgagcagc ccgctgattc aaagcctgcg    2880
cagcgagcag gtgcgtctga ccagcgagta ccagcagaaa ctgtcgacct tcaagccgga    2940
ttacccggag atgcagcgcc tcaaggcgca gatcgaagag tcgcgtcgtc agatcaatgg    3000
cgaagtcatc aatatccgtc agtcgctgaa ggcgacctac gacgcctccg tgcatcagga    3060
gcagctgctc aacgaccgca tcgccggtct gcggtccaac gagctggatc tgcagagccg    3120
cagcatccgc tacaacatgc tcaagcgcga cgtcgacacc aaccgccagc tctacgatgc    3180
gctcctgcag cgctacaagg aaatcggcgt ggcgagcaac gtgggcgcca caacgtgac     3240 catcgtcgat accgcagacg tgcctacgtc taagacttcg ccgaaactca aattgaacct    3300
cgcgttgggc ctgatctttg gcgtattcct gggcgtggct gtggctctgg ttcgctactt    3360
cctgcgtggg ccttctccga ggtcgcggtt gaactgacat cgtgatgttg caaaacgatg    3420
gttaattgaa gtgacaactg attcagcgtg gaaaggtgg gatcccgtaa ggtgcgggct     3480
ccctcgtttg aaggtttgtc tctgttgaaa caaagggctg tcgtgcgatc tggggtcggt    3540
aggtattacc gcggtgatcg gacgacagga tgattgaaag ctcgcgtgcg attcgtatgt    3600 tccccccgcat gcgccgtatc gagtttggag gacatcccca tgcttttggc agacttgagt    3660
agcgcgactt acacgacatc ctcgccgcga ttgttgtcca aatattcggc agccgccgac    3720
ctggtcctgc gcgtgttcga cctgaccatg gtcgttgcgt ccggactgat cgcataccgc    3780
atcgttttcg gtacctgggt acccgcagcg ccttatcggg tcgcgattgc gacaacgttg    3840
ttgtactcgg tgatctgctt tgcgttgttc ccgctgtatc gcagctggcg cggcgtggc    3900 ttgctgagtg agctggtggt gctgggtggc gcattcggcg gtgtgtttgc gctgttcgcg    3960
gtgcatgccc tgatcgtgca ggtgggtgag caggtcgcgc gtggttgggt cggcctgtgg    4020
ttcgtcggcg gcctggtgtc gctggtggcc gcacgcacct tgctgcgtgg cttcctcaat    4080
cacctgcgca cgcagggcgt ggatgtccag cgtgtggtgg tagtgggcct gcgtcatccg    4140
gtgatgaaga tcagtcatta cctgagccgt aatccctggg tcggcatgaa catggttggc    4200
tatttccgca cgccgtacga tctggcggtg gccgaacagc gccagggtct gccgtgcctg    4260
ggtgatcccg atgagctgat cgagtacctg aagaacaacc aggtggagca ggtgtggatc    4320
tcgctgccgc ttggcgagcg cgaccacatc aagcagctgc tgcagcgcct ggatcgctac    4380
```

-continued

```
ccgatcaacg tgaagctggt gcccgacctg ttcgacttcg gcctgttgaa ccagtctgcc      4440
gagcagatcg gcagcgtgcc ggtgatcaac ctgcgtcagg gtggcgtgga tcgtgacaac      4500
tacttcgtgg tcgccaaggc gctgcaggac aagatcctgg cggtgattgc gctgatgggc      4560
ctgtggccgc tgatgctggc cattgcggta ggcgtgaaga tgagctcgcc cggcccggtg      4620
ttcttccgtc agcgccgcca cggcctgggt ggccgcgagt tctacatgtt caagttccgc      4680
tcgatgcggg tgcatgacga tcatggcacc acgattcagc aggcgaccaa gaacgacacg      4740
cggattacgc gcttcggcag tttcctgcgc cgcagcagcc tggacgagct gccgcagatc      4800
ttcaatgtct tgggtggcag catgtcgatc gtgggcccgc gcccgcacgc cgcgcagcac      4860
aacacgcact atgaaaagct gatcaaccat tacatgcagc gtcactacgt caagccgggg      4920
attaccggtt gggcgcaggt caacggtttc cgcggtgaga ccccggagct gcggacgatg      4980
aagaagcgca tccagtacga ccttgactac atccgtcgtt ggtcgctgtg gctggatatc      5040
cgcatcatcg tgctgacggc cgtgcgcgtg ctcggacaga agaccgcgta ctgatgacgg      5100
tggggagtgt gcgacctggc gcaccttgcg ccgcgggcgg ctgcatcgca gccgcctttc      5160
tctcgcgggc gctgacatgc tgattcaaat gagcgagcag gcgcgggtgc gttggcacaa      5220
cgcgctgatc gagctgaccc tgctgaccgg cgtgggctac aacctgctgc tggcgttgat      5280
caacgccaac gtgttcaccg tacgtccggt gatcacatat gcagtggaat tctggtcta       5340 cgcagcctgt ttcctgctcg gctgggctc gatgagccga cagcgcatcg cgatgatctt      5400
cggcgggcta ggcttgatcg tgacgctgat gttcgtgcgt ttcctggtca actggcagat      5460
cgaccccaag ttcttccgcg atgccctggt ggtctttgca tttgtcgtgc tggggtctgc      5520
ttacaccggc tcgttgccca agctgttcat acgcatgacg atcatcgtgt cattggtcgc      5580
tgcgttcgag ctggcgatgc cctcggctta tggcgatctg gtcaacccga agagcttctt      5640
cgtcaatgcg cgcggcatga gtgcagaagg gttctggaac gaggacagca atctgttcgt      5700
cagtgccaca cgacccggtg agcgcaactt cctcccaggc tcgaacctgc cacgcgcctc      5760
ttcctggttc atcgagccgg tgacgatggg caattacatc tgcttcttca ccgcgatcgt      5820
attgacgttc tggcgctgga tcggccgtc gatgctgatt ctgtctattg gattgatcgg      5880
cttcatgatt gtggcatccg acggccgact ggctgccggc acctgtgtgc tgatggtgct      5940
gctgtcgccg ttattgaaac ggatggatca gcggttggcg ttcctgttgt tcctgttttgt      6000 gatcgcctct gcctggctgc tggtgtggat gaccgggatt acggcctacc aggacaccac      6060 gatgggcgc atcttcttca ctgtgaattc gatgaacaat ctatcgttcg agtcgtggat      6120
gggcctggat tttgcgcagg cctaccgta tttcgacagc ggtatttctt actttattgc      6180
ttcgcagtcg attgtcggcg tgctggcgtt cctgctgtct tattcgttcc tgctgctgat      6240
gccgagcaag gaagggcagt tgttcaaaaa ccaggcgatg tttgcctttg cactgagcct      6300
gttggtgtct aacggctatt tctcgatcaa gacatcggcg ctgtggtggt ttgtctgcgg      6360
ctgcatgtgg cacctgatgc cagcagcgtc agccgtgccg gtgcgcgacg aaagcaagga      6420
agatccaacg gacaacggcg tgcatgtgcc gttgcccgca ggagcgccgc ggtgaatacg      6480
gtgacagggg catcggggac gtcggcgcct gtgcaggctg ccggcgcgcg tgccttcgcg      6540
agcggccgta gccgcgatcc acgtatcgat gcgaccaagg cgatcgcgat attgctggtg      6600
gtgttctgcc acgcaaaagg cgtgccgcac ggaatgaccc tgtttgccta cagcttttcac      6660 gttccgcttt tcttcctcgt gtcgggttgg ctggctgccg gttatgcctc gcgcacaacc      6720
```

-continued

```
agcctgctgc agacaatcac caagcaggca cgtggtctgt tgctgcccta tgtcgtgttc    6780
tatctgcttg gatatgtgta ttggctgttg acgcgcaaca tcggcgagaa agctgcacgt    6840
tgggggagcc acccgtggtg ggagccgatc gtgtcgatgt ttaccggcgt cggcccggat    6900
ctgtatgtgc agccgccgct gtggttcctg ccggtgatgc tggtcaccgt gattggctac    6960
gttctgttgc ggcgctggat gccgccactg gtcattgcgg ctgtcgcagt tgttctcgcc    7020
tggttctgga tgaactggtt tccgctccag cacatgcgat tgttctgggg cctggatgtg    7080
ctaccggtgt cgctgtgctt ctacgcactg gcgcgctgc tgatccacgt gtcgccgtat     7140
cttccaacct ccttgcctgg tagcgcgttg gtcaccgtag tgctggcagc attggttgcc    7200
tggctggccg gggtcaacgg ccgcatcgat gtcaacatgc tggaattcgg aaggcagcat    7260
gccgtattcc tgttgagtgc agtggcgggt tcgttgatgg tgatctgcgc ggcgcgcatg    7320
gtgcaggaat ggacatggct gcagtggatc gggcgcaaca ccttgctgat cctgtgcacg    7380
cacatgctgg tcttctttgt actgtctggt gttgcggcct ggcgggtgg gtttggtggg     7440 gcgcgcccag gccttggttg ggccatcttc gtgacgctct ttgcgctggt cgccagcgtt    7500
ccgctgcgct ggtttctgat gcgttttgcc ccctggacct tgggtgcacg tccggtgtcg    7560
gcatgacgac ggctgcgatc actgccggtc gcgtcgacac aatcgcctca actgtcgcgg    7620
agcgcgactg gcagatcgac gtggccaagg ctcttgcgat cattctggtc gcgctggggc    7680
acgccagtgg catgccgcct gcctacaagc tgtttgccta cagcttccat gtgcctctgt    7740 tttcgttct ttccggctgg gtcggtgaac gcttcgggcg tcgtgcattt ggccggaaga     7800
cggtgggaaa gcttgcgcgc acgctgctga ttccctacgt cagctttttt ctggtggctt    7860
acggctactg gatactgagc gcagtgctca acggcacatc ccagtcctgg gctggccacc    7920
cctggtggca tccgtttgtt ggattgctgt gggccaatgg atccagcttg tatgtgctcc    7980
cggccttgtg gtttctcccc gcactgtttg tcgccaccgt tgtctacctg gcactgcgcg    8040
aagacctgag cgccgcagtg ctcgcggtct gcagtttgct ggttgtgtgg gcgtggacgc    8100
gttggttccc agggctgcgg ctgcgccttc cgttttgcact ggatgtgctg ccggtcgcgc   8160
tgttcttcat tgcagtcggc gcatggctgt cacgcttcgc agagagagtg cgcgcgcttc    8220
ctgcggtcgt ttgggtcgtc gcgttccggg tcctggcatt cgcctggggg ggcgttgcag    8280
ccatgaacgg gcaggtggat gtcaataatc ttcagttcgg aaaatcgtcg ctcctgttcc    8340
tgatcgcaag cctgctgggt acagcaatga cgttgtgcat tgcctacttc atgcaagggt    8400
ggcgctggct gcgttggatc ggcgccaata cgctgctgat ccttggcacg cacacgttgg    8460
tgtttctggt cgtgaccagt gtcgtggtgc gaaccggggt gatcgatcgc aaactcatcg    8520
gtacacctgt ctgggcgctg gctctctgcg cctttgccat cgctgcctgc attcccatgc    8580
gtgccgtgct ggtgcgccgc gccctggatg ttgggattga aacgcaagtg agacattttc    8640
agaatcatca gtcgatgtgg cgtgttcgtg tgagtcaccg gcaaaggaga tcggcgcaat    8700
gaaagtcgtg catgtggtcc gccagttcca tccgtcgatc gggggatgg aggaagtcgt     8760 gctgaacgtg gcacgtcagc atcaggccaa cagtgccgac acgttgaga tcgtgacgtt     8820 ggatcgtgtg ttcaccgatc cctctgcgca actggcgcag cacgagctcc atcagggggtt   8880 gtcgatcact cgcatcggct atcgtggttc atcgcggtac ccgatcgcgc cgtcggtgct    8940
gggggcgatc cgttcggcgg acgtggtgca tctgcatggc attgatttttt tctacgacta   9000 cctggcgttg accaagccgc tgcacggcaa gccgatggtg gtctcgacgc atggcgggtt    9060
tttccacact gcctatgcgt cgcgcatgaa gcagatctgg ttccagacgc tgacgcgtac    9120
```

-continued

```
ttctgcgctg gcctatgcgc gtgtgatcgc cactagcgag aatgacggcg atctgttcgc    9180
caaggtggtc gcgccgtcgc gcttgcgggt gatcgagaac ggtgtcgacg tggagaagta    9240
tgcagggcag ggcgctcgag cgccgggacg gaccatgctg tatttcgggc gttggtcggt    9300
caacaagggc ctgatcgaaa cgcttgaatt gctgcaggct gcgctcacgc gtgatccgca    9360
gtggcggttg atcatcgccg ggcgcgagta cgatttgaat gaggcggatc tgcgcaaggc    9420
catcgccgaa cgcggtttgc aggacaaggt gcagctgagc atgtcgccat cgcagcagca    9480
gttgtgcgcg ttgatgcagc aggcgcagtt cttcgtgtgc ctgtcgcggc atgagggtt    9540 tgggattgcg gcggtggaag cgatgagcgc ggggttgatc ccgattctca gcgacattcc    9600
tccgttcgtg cggcttgcca ccgagtccgg acagggtgtg atcgtcaatc gcgacaggat    9660
tcaggccgcg gccgacagcg tgcaagcatt ggcgctgcag gccaatgcgg atttcgatgc    9720
gcgccgcacg gcgaccatgg cgtatgtggc gcgctacgac tggcggcacg tggtggggcg    9780
ttatatcgac gagtaccacg ctgcgctggg aacaccacgt acgcaggagg ccgtgcgatg    9840
agcgcgtctg cttcgctgcc agtgacgcgt gctgctgcgg cgccccggat acgtgctg    9900 ttctccaccg aaaagccgaa cgccaacacc aacccgtatc tcacccagct ctacgatgcg    9960
ctgccggacg cggtgcagcc gcgcttcttt tcgatgcgcg aggcgttgtt gtcgcgctac   10020
gacgtgctgc atctgcactg gccggaatat ctgctgcgcc atcccagcaa gatgggcacg   10080
ctggccaagc aggcctgcgc tgccttgctg ctgatgaagt gcagctgac cggcacgccg   10140 gtggtacgca ccttgcacaa cctggcgccg catgaagacc gcggctggcg ggagcgcgcg   10200
ctgctgcgct ggatcgatca gctcacgcgg cgctggatcc gcatcaacgc cactacaccg   10260
gtgcggccgc cgttcaccga caccatcctg cacggccatt accgcgactg gttcgcgacg   10320
atggagcaga gcaccacgtt gcctggtcgg ctgctgcatt ttggattgat ccggccgtac   10380
aagggcgttg aggtgttgct cgacgtcatg cgcggatgtg caggacccgc gcctgagcct   10440
gcgcatcgtc ggcaacccgg cgacgccagg atgcgcacgc tggtcgaaac cgcctgcgcg   10500
caggatgcac gtatcagtgc actgctggcc tatgtcgagg agccggtgct cgcgcgcgaa   10560
gtcagtgcct gcgaactggt ggtactgcca tacaagcaga tgcacaactc cggcaccttg   10620
ctgctggcgt tgtcgttggc gcggcccgtg cttgcgccgt ggagcgaatc gaacgccgcg   10680
atcgccgacg aagtcgggcc gggttgggtg ttcctgtacg aaggcgagtt cgatgcggcg   10740
ttgttgagcg gcatgctcga tcaggtgcgc gccgcgccgc gtggcccggc gcccgatctt   10800
tcacaacgtg attggccacg gatcgggcaa ttgcactatc gcacctactt ggaagcgctc   10860
ggcaaggatg gagacgccgc gctgtgaccg cagagacatc gaccatgact tccccaacac   10920
cgccgccgcg cagcctcggg tcgcgtgccg ctggcgccgc cgtgaccatg atcgggcagt   10980
cggccaagat gatcgtgcag ttcggcggca tcgtgctgct ggcacgcttg ttgacgccgt   11040
acgactacgg cttgatggcc atggtgaccg ccatcgtggg ggccgccgaa atcctgcgcg   11100
acttcggtct ctccgcagcc gccgtccagg cgaaacatgt cagccgcgag caacgcgaca   11160
acctgttctg gatcaatagc ggcatcggtc tgatgctgtc ggtggtggtg ttcgccagcg   11220
cgcactggat tgcggacttt tatcacgagc ccgcattggt gacgatttcg caggcattgg   11280
cggtgacctt cctgctcaac gggatgacca cccaataccg cgcacacctc agtcgggggc   11340
tgcgcttcgg tcaggtagcg ctgagcgatg tgggttcgca ggtgttgggg ttgggtgctg   11400
cagttgcggc cgccttggcc ggctggggct actgggcgtt gatcgtgcag caggtggtgc   11460
```

-continued

```
aggccatcgt gaacctgatt atcgctggcg catgtgcacg ctggttgccg cgcgggtacg    11520
cgcggcaggc gccgatgcgc gatttcatga gctttggctg gaacctgatg gcggcgcagc    11580
tgctcggcta tgcgagccgc aacgttggcc aggtgatcat cggctggagg accgggcccg    11640
acgcgctggg tctgtacaac cgtgccttcc agttgttgat gatgccgttg aatcagatca    11700
atgcgcctgc gactagtgtg gcgctgccgg tgttgtcgca attgcaggat gagcgcgagc    11760
gctacagcgc ttttctgttg cgcggccaga cggtcatggt gcatttgatc tttgcgctgt    11820
tcgcgtttgc ctgtgcactg gccatgccgc tcatcgtcct ggtgctgggt gagcagtggc    11880
gggaagcggt gccgctgttt caggtgttga cgctgggcgg tatcttccag acggcgtcgt    11940
acgcaaccta ctgggtgttc ctgtcgaagg ggttgatgcg cgagcagttg gtgtattcgt    12000
tggtcggtcg catcctgctc atcgcctgca tttttgttgg ctcccgctgg ggggccatgg    12060
gcgtggcgat cggctactca ttcggcctgc tgttgatctg gccgctgtcg ctggtctgga    12120
tcggcaagat cacggacgca ccggtcggtg cgttgttcgt caatgccatg cgtgcgctgg    12180
tggcctacgg tatcgccggc ggctgcgctt attacgcatc ggtcactgtc ggtggtccat    12240
tgtggcagca gctgctggtc ggcgccggcg cgatggcgct ggtctgtctg ctcgcattgg    12300
catggccggg attccggcgt gacgtggtcg ctatcgtcaa tatccgcaag ctgctcacgc    12360
aggcgaaggc gcgccgatga cactgcactg cggtactgga atgttggact tcgaaacttc    12420
ccactcttgc aaaggacacg gcctatgagc gtctctcccg cagctccagc ttccggcatt    12480
cgccgtccct gctatctggt cttgtctgct cacgatttcc gcacgccacg tcgggctaac    12540
atccatttca tcaccgatca gttggctttg cgtggcacga cgcgtttttt ttcgttgcga    12600
tacagcagac tctcccgcat gaagggagat atgcgcctgc cgctggatga caccgcaaat    12660
accgttgtct cgcacaacgg tgtggactgt tacctgtggc gcacgacggt gcatccattc    12720
aatacacgcc ggagctggct acgtcctgtg gaagacgcca tgttccgctg gtatgccgcg    12780
catccgccaa agcagttgct ggactggatg cgcgagtccg atgtcatcgt gtttgaaagc    12840
gggatcgcag tcgcattcat cgagcttgcc aagcgggtca atccggctgc caaactggtc    12900
tatcgcgcgt cggacgggct gagcaccatc aacgtggcgt cttacatcga gcgcgagttc    12960
gaccgcgtgg ctccgacgct ggacgtcatt gccttggtgt cgcccgcgat ggccgcagaa    13020
gtagcaagcc gcgacaacgt cttccatgta ggtcacggcg tggaccacaa cctcgatcag    13080
ctcggcgacc cgtcgccgta tgccgaaggc atccatgcag ttgcggtcgg gtcgatgctg    13140
tttgatcctg aattttttcgt cgttgccagc aaggcctttc gcaagtgac cttccacgtg    13200 atcggctccg ggatgggccg ccatccgggc tacggcgaca atgtcattgt ctatggcgaa    13260
atgaagcacg cgcagacgat tggctatatc aagcacgcac gtttcggcat tgcgccttac    13320
gcgtccgagc aggtgccggt gtatctggca gacagctcaa tgaaattgct gcaatacgac    13380
tttttcggct tgccggcggt gtgcccgaat gctgtggtgg ggccgtacaa atcgcgcttc    13440
gggtacacgc caggcaatgc cgattcggtg attgccgcca ttacccaggc actggaagca    13500
ccgcgtgtac gttaccgcca gtgtctcaac tggtccgaca ccaccgaccg cgtgctcgac    13560
ccacgggcgt acccggaaac ccgtctttat ccgcaccccc ccaccgccgc gccgcagctc    13620
tcttcggagg cagcgctctc acattgagga ggcgcttttt tgatcacgtt tgaaggagga    13680
tccctgtcat ggccaacgct ttactgcaga aatgggtgga acgggcggaa cgtcgcgcat    13740
tgttctggtg gcagcccaaa aacggtggcg tgaacatggg ggatcacctg tcgaaggtga    13800
tcgtgtcgtg cgtgttggcg ttgcaggaca agacacttct ggaaaacgc gatttgcgcc    13860
```

-continued

```
agaagctgat cgcaaccggg tcggtgctgc atttcgccaa agatggcgac accgtgtggg    13920
gaagcggtat caacggcaag attccggccg agcgcaatac gttcagcacg ctggacgtac    13980
gcgcggtacg cggtcccaag acccgcgcat ttttgctgga acgtggcatc gcagtgcctg    14040
aggtctacgg agacccggga ttgctgaccc cgatgttttt ccccgccgac gccctcggcc    14100
cggtcaccaa gcgcccgttc gcgatcgtgc cgcacttcaa cgagccggtt gagaagtaca    14160
gcgcctacgc cgagcatctg gtgtttccca acgtcaagcc ggccaccttc atgagtgcgc    14220
tgctgggtgc ggaatttgtc atcagcagtt cgctgcatgg cctgatcctg gccgaagcct    14280
atggcatccc ggcggtgtat ctggactggg gcaacggcga agaccgtttc aagtacgacg    14340
actactacca cggcaccggg cgcatgcaat ggcatgccgg ccacagcgtg gaagaatgca    14400
tggaactggg cggcaacggc agtttcgatc ttgaacgctt gcaggcagga ttgctggctg    14460
cgttccctta cgatttgtgg tgaaacgaca atgcatggcc agccagcagg tgtggagacg    14520
gcaacggtga gtgcagcgac acctgcgcaa ggggtggtga ttccgctggg cggcttcccg    14580
gtgttgtcga ccacgcagga agccttgcgc ctggatctgt tccatgcgct ggccgcgcat    14640
cagccgcgcc gggtgttttt cgcgaacacc aacttcatcg tgcagtgcca ggcgctgcgc    14700
gcgcgcatgc aggcgccggc agtgcgcatc gtcaacgatg ggatcggcat ggatctggcg    14760
gcgcgcctga tccatggccg ccggttcgcc ggcaacctca acggcaccga cctgattccg    14820 taccttttgcc gcgaggccgc gcagccgctc aagttcttcc tgctcggcgg ccgcccgggc    14880
gtgggcaaga ccgccgcggc gaccttgacc ggaacgctgg gccagcaggt cgtgggcatg    14940
tgcgatgggt atggcgaatt tgcggcgcg ggcgagggcc tggccgagcg catcaatcgc    15000
tccggcgccg atgtgctgtt ggtggccttc ggcaacccgc tgcaggagcg gtggatcctg    15060
gaccacagcg aggccttgca ggtgccgctg gtgttcggcg tgggcgcctt gctggatttt    15120
ctctccggca ctgccaagcg cgcgcccaac tgggtgcgcc gtttgcatat ggaatggatg    15180
taccggctgc tcaacgagcc gcgccggttg ctcaagcgct acagctggga tctgctggtg    15240
ttcttccgca cctgcctgcg tgcgggcaaa cagctggcgt gatgcacggc ggcggtgtgt    15300
ggcctagcat gcgtgcatgc atccaaccgc cgccgcgctg attcgaacat tgggccttgc    15360
cccccatccg gagggcggcc actaccggcg cgtgtacgcg tcgacgcgcc aggtgctgga    15420
tgacagcggt gcgccgccgc gtccggcgct gaccgccatc cgcttcctgt tgtgcgcagg    15480
cgaagccagt cgctggcatc gggtggatgc cgaggagtgc tggcactggc agcaaggtgc    15540
gccgctggag ttgctgatct tcgacgaagc gagcgggcag ttgcggcgcg aagtgctgga    15600
cgccgcagag cgcggcgacg ccatgcacgt ggtgccggcc ggctgctggc aggcggcgcg    15660
ctcgctgggg gacttcaccc tggtgggctg cacggtttcg ccagggtttg tctgggaagg    15720
tttcgcgctg ctcgaagacg gctcgccgct ggcggcacga ctggccgcgt tggttgccga    15780
aggcgccgcg ccggagccgc caacgcttcc ctaacgcgtg cgggcccgcg ttcgcgtagt    15840
gtccgcgttc caaccgggag gcggtacgtg atgcagcgca gggggcggt gtggcgggca    15900 ggaatcgcgt tggtgtcgtt gttggcaccg atgctggcgt gtgccgtcga ggtggccgta    15960
caggcgccgc cagcgccgcc aacggtggtc gatctggaag ccatggtggt gcgcgggcag    16020
caacccggcc ccggcctgtg gaaggtcagc aagggcgacc acgtgctgtg gatcc        16075
```

<210> SEQ ID NO 2
<211> LENGTH: 28804
<212> TYPE: DNA

<213> ORGANISM: Sphingomonas sp. S88

<400> SEQUENCE: 2

| | | | | | |
|---|---|---|---|---|---|
| ggatccactg | gccgggaatt | gccgagaatc | ctccgatgaa | gcgctcgtcg | ggtaccagcg | 60 |
| tgccccgggg | cgcatcgctt | tgcgccggcg | catcgccgcc | gctgccgggc | cggccattcc | 120 |
| agcgggtcc | gggctgcaaa | atccccgggc | ctgcctttac | gccatgcccg | gcagccgagc | 180 |
| tgccgggcgc | cgagcatgcg | agcggcgtaa | ccgataggc | gaggcccccg | cccagaaggg | 240 |
| tgcgacgtgt | ggtatcgatc | atgcggcgcg | ctccaaaccg | tgcgcgccgt | gactacaacc | 300 |
| aaaaatgctg | cgctgcgagc | gggatcaggc | gccccgtgcc | tgcttcgagc | ggtacagcag | 360 |
| cgcgaacgtc | agcccacca | gcatgaagaa | gacttggtcg | ttgtcggtct | gcgacagcac | 420 |
| gagcctggta | ttgagcagca | cgaccatcgt | cgtcgcgacc | gccagatgca | gcggatagcc | 480 |
| ttgggagggg | tccgtcaacc | cggcgcggat | caacagcccg | gcacccagca | ccatcgtacc | 540 |
| gtagaatgcg | atgaagccga | gcaccccgta | atcgacggcc | gtcgaaagga | agccggagtc | 600 |
| gatcgacagg | aacccgctct | gggaacgcca | tccgacgacc | tccgcggact | ggaacggccc | 660 |
| gtagccgaat | accgggcgca | tcgcgagctt | gggcaagccc | atgcggatct | gctcgtggcg | 720 |
| cccgtcgttg | ctcgcctggg | tcgcgccgcc | gccaagaacg | cgattgtgta | ccgcaggcac | 780 |
| taccatgatc | atcaccgcga | gaaccacggc | gaaggccgga | tacatcatcg | tcgtggaaat | 840 |
| cccgacgagc | ccgccacgct | ccttgatcca | gcgccgcagg | ccccagagca | acagataggt | 900 |
| ggcatgcgcc | acgaccatgc | cgaccatgct | caggcgcgcg | ccgctccaat | aggcggacaa | 960 |
| taccatggcg | agatcgaaca | ggatcgtgag | tgccagcgcc | gacaccgacc | ggctgttcac | 1020 |
| catcaggtgg | atcgcgaagg | gaatcgtcat | cgccacgagt | tcgccccaca | ccagcgggtt | 1080 |
| cccgaacacg | ttcatcacgc | gatacgtgcc | gcgcacctgc | gaggtgagat | gcaggatgac | 1140 |
| gctcggatcg | ttgatctgca | gccagctggg | aatgtggccg | acccacagaa | cgtgctcggc | 1200 |
| ccggaactcg | aagaagccga | tcaccatcag | cacggacacg | cagcccagca | tgttccgcac | 1260 |
| ccaccattcg | ggtgtgcgcg | tgttcgatcc | caggcaccac | agcgtcgcga | agaagaacgg | 1320 |
| cgtgaccgtc | agcgagatat | tcaccaggcg | cccgatcgaa | acggatggct | ggctggaaat | 1380 |
| gagcgacgcg | atgatctgga | tgatcaggaa | gcccagcatg | aagcgggcaa | gccagggcga | 1440 |
| cgccgacagc | gtcaccgcca | tgtcgcgccg | aaacttcggc | gaaatcgaat | agcacaccag | 1500 |
| cagaagaagc | gtcgtcagca | cgccgaacag | gcggcggaag | gagatccagg | gcaggcccgc | 1560 |
| caccgacagc | gacagatagt | tcggccacac | gatcgcgagg | atcatgaaca | ggacgtagca | 1620 |
| gcgcagcagc | aacttggtgg | gcgccttgtc | ggcctccggg | agcgcccaga | tgacgaacag | 1680 |
| cgcgaggatc | gccagcggcg | cggcggcccc | gaggagcatg | ctgggcggca | ggatcgccga | 1740 |
| aagcagcccg | tagaccatcg | acacgaacac | gatcacggcg | agcccgatga | agcgccgccc | 1800 |
| gagcgtgacg | agaccagagc | gttgcgggtg | atagagcggg | agcaccgctc | tggcggggaa | 1860 |
| gaacacgatg | tcgcgcgccc | ggcgcagggg | ctgcaccacc | cgcgccaagc | cgccgctccc | 1920 |
| ccgaactcgc | gccgatgtcg | ccatgaccaa | cccctagat | aatcggtatg | ccgatcagcc | 1980 |
| gcaccgcgac | catcgacacg | aagcgcagga | agaccgacgg | caccgcgatc | gcaatcgccg | 2040 |
| cgcctagtgc | accatagggc | ggaatcagga | ccagcgcgag | tattgcggca | aggataaccg | 2100 |
| acgacatggt | cagcaccacg | gccagacgct | cgcgattggc | catgacgagg | acgccgccgc | 2160 |
| tcgacgcgaa | gaccatcccg | aacacctgcc | caagcaccag | cacctgcatc | gcggcggcgc | 2220 |
| ccgcggtgaa | ctgtttgccg | aacaggccca | tgatccaatg | cggagcgacc | agcaccgcca | 2280 |

```
gggcgatggg cgaggcggcg accagcagcg cgagaatggt gatccggatg atgcgggcga   2340
tccgcttgac gtcgccctgt tcgtaggagg cggcaaagac cggatgcagg atcgtctcgg   2400
aggtggccga cagcaacttg agcgaggatg cgatctgata gcccacccgg aacagaccgg   2460
cttcggcggg gccgtgcgtc gcggcaagga tcacggtggc aaaccagtcg acgaagaagt   2520
tgttgacgtt ggtgatcagc accatgaagc cggggcgaag catcggccgg tccaacggct   2580
cggccggcgc ccaatcacgc gtcatgcggc ggacgatgat cgtcgcggca acatcgtca    2640 ccagccagcc gaccaggtac agcaccgacg gcagcagcgg attatgggca acgccgatca   2700
gcagcgcgcc ggccagcatc gccccaccca ggaaggtgcc gagcggccca tcgaccatct   2760
gcgacttgcc gatatccccc atgccgcgca gcgtcgtcga agcgagacgg caataggcgc   2820
tgaccggaat gagaaacccc atgatcagaa ggtccggcgc catggcgggg ctgcccagca   2880
ggttggtggc aatctgttgg tgaaacagca ggatcatcac catcaggacc aggccaccac   2940
ccaccgcgac ccgcgtggca tgccgcactg cggtacgcgc cacaccgtc cgattttgcg    3000 acacgcagac ggccacggtg cgcaccagga tggtatcgag gccgatcagc gacagaatga   3060
ccagcatctg cgcagtcgtg agcgccgtac cgaaggcacc gacgccggcg ggccaaagg    3120 cgcgggcgac cagccaggtg aaagcgaaac tggtgacggc gccgaagccc ttgacgccga   3180
agccgaccac catctgcccc cgcagccccc gcaggtgcaa cttgctacgt gtcacgttga   3240
atgcttgccc cacaggagat cccgtctgtg ccttatggca gggccctccc gggggcaagc   3300
ctgaggacgt catcagacgt gatagaagtc ctgcaccaac ttcttggtgg cgaacaggct   3360
attcgccacg gacaggctgc ccgtcgccga gacggccgca gtgccggccg cattcatggc   3420
gatcgcctgg gcgagcgaca cttgcgcgac ggacgccgtc gatgccgatc cccccagcgt   3480
cagcgtgccg gtggtcgccg ccggcagcgc cgtcgacgtg accggggtgc cgagaatggt   3540
tacggcgctg gcggccaagc tgctggtgag gctgggcttc acggtggtgg tcggctggct   3600
ggcggcggtc gccgcggcat tcagcgcaag gatctgggac gcactgaggg cagcgtcgcg   3660
catctcgatc tcgcccacgc tgccgctgaa gacagcgttg aacgggctgc cgatgtacag   3720
tccggcatat tcgaccgccc gcgtgctgcc gacgatcgtt cccgatccct tcaccacgcc   3780
atcgacatag atgatcgcct tgcccttcgc gctgtcatag gtcagcgcga tcttgtgggt   3840
ggccgtgtcg gtcatcttgg cgccgctcgt cgcgacggta tagctctgcc cggcggcatt   3900
cttgacggtg aagaccagtt cgccgtccgc ccggagcgag attccccagc tctggttgac   3960
gcccatgatc tggccgaccg cgcccgtcgc ggtggcacgc ttcatgtcga agttgagcgt   4020
gaaggcgggc agcgcgaaga gttgacgtga attgtcccgc gtaagctcga agccggtgcc   4080
ggtcttcacc tggaacatgc cgttgctgat ggcggtgaga tccagcgcct tcgtggtctc   4140
gtccgtgctc cagcgcgtct ggtccacgat tccggtcgca gtgaactgca gatccagcag   4200
caggttggcg ccggtcgagg tctgtgctgc cgcctgctcc ttggcgacct gcgcggcaaa   4260
cgcgctgcct gcaggcggct gatacccgac accactgacg atcaggttcg ccagttgcgc   4320
cttcgatccg gccatgagat cgccgatctt gcgaagagtg accgcgtccg ttgcaagcac   4380
ggcgttgttc gattgagtaa tgccgctcga cgttgcggtg atgacaacct ggtccacgac   4440
attgttggtg accttgccgc cggtcacgcc gtccaggcgg atccaatcgg cgatcgcatc   4500
catcttcgag atgatggtat tggagtccac ggtgacgttc ttgcccagaa cgacattgat   4560
gccgtgcgtg aaaccattct ggtacacgag attgtttttg atcgtgatgt tttcgtaggg   4620
```

```
aatgctggat tcattgccca tgaatacgcc ctggaaggcc aggccgtccc cctgcatcat    4680
cacgttattg gtgatcgtga tgttcgtgtt gcccttggtc ttgccgttcg tcatgaactg    4740
gatggcgtcg ggatgctcac cattcaccgg atagaggttg gtgaacatgt tgttgtcgat    4800
gacgacgttc gacgcttcgg cgaaattggt gtgatcgcgg cgattgtcgt ggaagttgtt    4860
gccctgcagg gtgacaccgt cgacggtgag gacgttcatc cccagggcga aatgatcgac    4920
cgaggaattc ttgatcgtca ccccttgct ttctcgcagc agaagccccc agcccatcga    4980
cttcgtcaca tcgcccgtac ccccgctcag ggtcacgccg tcgatcacga cattgctgga    5040
gccgatgatc cggttcgcgt aattatagtc ctgtgccggc tggaagtttt gtgcggccgt    5100
gacgttcttc accaccaggt tgctgctgtt gatgatctgc agggtcgtca cattcaccgg    5160
cttgctcgca tcgagcgagg tgatcgtgac gggcgtggtg aaggtcgtgg tgtgcacggt    5220
gatggacgta taggtccccg ccgcaagctt gatcgtctcg cccccttcg cagccttgat    5280 ggcggcgtcc agttcgctct gattcctcac gatgatgtcc ggcatgtact ctaccctcgt    5340
tacgcgtcga ccccaatcga cctgcgatcc ctcggaccgt cttgtacctg ccaagccctg    5400
aaacggtggc taagaggcag ggttaatgcc ctgtttttca agccgataac tggcagccct    5460
caaggcactg ccagcgtgcg ggcaacactc tcgacgccgc agtgcagcac gggtaagaac    5520
gaggcatgga agcctcgccc acacccgacg tcagcatcct ggtggttgcc taccactcgg    5580
ctccgttcat cggacaatgc atccggggca tcgccgcggc ggcacaaggc acagcccacg    5640
aaatcctgct gatcgacaat ggcggcggcg acaccgaggc ggtggttcgt gccgagttcc    5700
cgcacgtgcg gatcgtgccg agcgagggca atatcggctt cggggcgggg aataaccggt    5760
gtgcggccca tgcccgcgcg ccgcggctgc tgctcgtcaa ccccgacgcc attccccgcc    5820
ccggcgcgat cgacctgctg gtcgccttcg ccaaggcgca cccggacgcg cagcctggg    5880 gcgggcgttc ctattttccg aacggccagc tggaccatgc caacttcctc ccgctgccca    5940
cggtgcgcga tttcgtcgtg tcgatcttca gcagcagccc gatgcggcgc ggcggccttc    6000
ctgccgacgc caccgcgccc gggccggtcg aggtgctcaa cggcggcttc atgatggtcg    6060
atgcccgcgt gtggcgggag atcgacggct tcgacgaagg cttcttcctc tattcggagg    6120
aaatcgatct gttccagcgg atccgcgcgc ggggctattc cgtgctggtc gatccggctg    6180
tgggcgtggt gcacgacacc ggtggcgggc attcgctctc gcccactcgc gtgctgtttc    6240
tcaccaccgg ccgcatgcat tatgcccgca agcatttcgg ccacgtcggt gccgtcgtga    6300
cgggctgggc actgtgggcc aatgccgcca aatatgtcgt tatcggcggc ctgctcgggc    6360
gcctctcacc ccgccgcgcg gcgcgctgga acgcgctgcg cgatgcctgg agcatcgtgt    6420
tcggccagcc gcggcgctgg tggcacggct ggcgcgacca cgttcgtact tgaggatagc    6480
gccgcgccag acgcccgaa atggcaaccc gacgcaaggc ggaaggcttg ccgacggcaa    6540 gcccccgac ttgtcgctca ctgcgcggcg ttgggcgccg gagcaggggc gcagcaggc    6600 gcggcggcag cgccgccctg cagttgcggc ggcgggctgt agcccggctg atatttcacc    6660
gactcgcgcg ccttcttcag acgatcgttc agctgcgcgt ccgccgcctt gctgaaccgc    6720
tcggtgcgca gcgtattgag cgcgagttcg cgcgcctgat cgcccgccag cggctggatc    6780
gtcgtgccgg tgatgacatt ggcggtgacg ccctgctgcg tcggcaggat gaacagctcc    6840
tgcgccggca gcgccgcaat cttgcggcgc atctccggcg gcaacgcggc ggtgtccagc    6900
tgggtcggcg cgcggcggaa ctgcacgccg tcggcggtca gcttggcggc aagctggtcc    6960
aacgtcttga gcggcgcgaa ttccttgaac ttcgccgccg agccgggcgg cgggaagacg    7020
```

-continued

```
atctgttcga tgctgtagat cttgcgctgc gcgaagcgat cgggatgcgc cgcttcatat    7080
tgcgcgatct cggcatcggt cggctgggcg atgccgccgg caatcttgtc gcgcagcagc    7140
gtggtgagga tcaactcgtc ggcgcggcgc tgctggatca ggaagacggg ggtcttgtcc    7200
agcttctgct cgcgggcgta cttcgcgaga atcttgcgct cgatgatgcg ctgcagcgcc    7260
atctgctcgg caagcttgcg gtcggtcccc tgcggcacct gcgtggcctg cacttcggca    7320
ttcagttcga agatggtgat ctcgtcgccg tccacgctgg cgacgacctg ccccttatcg    7380
agcttgcctt ccttgctgcc acatccgagg acggccagcg cggccgcagc caccgccgtt    7440
accaggtaca atttcttcat gaagacctcc cagccggcac ggaattgcgc acggcacaaa    7500
cttctacttg aacctattcg ggcgggcggg catccgcaat agcgttggca gtgcagcatg    7560
cctcccggcg ggaggcaggc gggatcaatg ggggacggca tggcagaagc gacggtgacc    7620
gaagcgaagg cgggcaaacc gctgaaaatg tgtctcgcag cttccggcgg cggccatctg    7680
cggcagatcc tcgatctgga atcggtctgg aaggaacatg actatttctt cgtgaccgaa    7740
gacaccgcgc tgggccgcag ccttgccgaa aaacactcgg tcgcgcttgt cgatcactat    7800
gccctcggcc aggccaagct cggccacccg ctgcgcatgc tgggaggcgc ctggcggaac    7860
ctgcggcaga gcctgtcgat catccgcaag cacaagcccg atgtggtgat ctccaccggt    7920
gcgggcgcgg tctatttcac ggcgctgctc gccaagctct cgggcgcaaa gttcgtccac    7980
atcgaaagct tcgcccggtt cgatcatcct tccgccttcg gcaagatggt caagggcatc    8040
gcgaccgtga ccatcgtcca gtccgccgcg ctcaagcaga cctggccgga tgcggagctg    8100
ttcgatccct tccgcctgct cgacacccc cgccctccca agcaggcact caccttcgcc    8160
accgtcggtg ccaccctgcc ctttccgcgg ctcgtgcagg ccgtgctcga tctcaagcgg    8220
gccggcgggc tgccgggcaa gctggtgctg caatatggcg accaggacct ggccgacccc    8280
ggcatccccg acgtggagat ccgccggacc attcccttcg acgacctcca gctgctgctg    8340
cgcgacgcgg acatggtgat ctgccacggc ggcaccggat cgctggtcac cgcgctgcgc    8400
gccggctgcc gcgtcgtcgc cttcccgcgc cgccacgatc tgggcgagca ttatgacgat    8460
caccaggaag agatcgcgca gaccttcgcc gatcgcggcc tgctccacgc cgtgcgcgac    8520
gagcgcgaac tgggcgcggc agtggaggcc gccaaggcga ccgagccgca gctcgccacc    8580
accgatcaca cggcgctcgc cggccgcctg cgcgagttgc tggcacagtg gagtgccaag    8640
cgatgagcgc gccgcggatc agcgtcgtca tcccgcacta caatgatccg gactcgctgc    8700
gacaatgtct cgatgcactg cagcatcaga cgatcgggcg agaggccttc gagatcatcg    8760
tcggagacaa caactccccc tgcggcctgg cggcagtgga agccgccgta gccgggcgcg    8820
cgcggatcgt cacgatcctg gagaagggcg ccggaccggc gcggaacggc gccgcggcgg    8880
aagcgcaggc cgagattctc gccttcaccg acagcgactg cgtcgtcgag cccggctggc    8940
tggccggggg cgtcgcccat gtcgccccgg gccgcttcgt cggcggccac atgtatgtgc    9000
tcaagccgga agggcgactg accggcgcgg aagcactcga gatggcgctg gccttcgaca    9060
atgaaggcta tgttcgccgt gcgaagttca ccgtcactgc caatctgttc gtcatgcggg    9120
ccgatttcga gcgcgtcggc ggatttcgta ccggagtctc ggaagatctg gaatggtgcc    9180
accgcgccat cgccacgggt ctcgcgatcg actacgcccc cgaggcctcg gtaggccacc    9240
cgccccggcc ggactgggca acgctactgg tcaagacgcg gcgcatccag cgcgagctgt    9300
tcctgttcaa tatcgagcgc ccgcgcggcc ggctgcgctg gcttgcgcgc tcgacgctgc    9360
```

```
agcctgcgct gattccggcg gataccgcca agatcctgcg cacgcccggc acccgcgggt    9420
cccgtatagc tgccgtcggc acgcttgtcc gcctgcgctt ctggcgcgct ggcgccggcc    9480
tcctgcaact gctcggcaga ccaatctgat gaaggcgggg cggccatggt gcggcgcccc    9540
gtctcctgtc ctcacaccgc cgcgagcgcc tcttccagcg tcccgctgtc gatccgcagg    9600
cgtcccacca tcagccagag atagacgggc agcgaatcgt cgttgaagcg gaagcggcgc    9660
tccccgtcct gcgcatcgct ctccaggccg agctggcggc tcagcgcgtc gagttcctgc    9720
tcgacctgcg ccgcagtgat cgtgctcccc ggcagcagct cgacgactgc ctggccggtg    9780
aaccaaccat cggtcgaacg cgacgcctcg cccagcgcgg cgaccagcgg atcgtagcga    9840
ccgccgacga acttgcgcat ctccagcacg gcgcgcggcg acatccggcc ttctatttcc    9900
aggatggcct ggtcgagcgc gcggcgcaga tgcccagat cgacggtcag ccgcccctgg     9960
tcgagcgcct cgagcgccgc atggtggcac agcagccgcg cgaaataggg cgaccccagc    10020
gccagcaggt ggatgatccg ggtgaggttc ggatcgaagc gcaggcccga ggcggtctcg    10080
ccgagcgcga tcatctcctg tacctcggtt tcctcgagcc gcggcatcgg caggccgatg    10140
atgttgcggc ggatcgaggg tacgtagccg acgagttcct gcaggttcga cgagacgccg    10200
gcgatcacca gctgtacgcg cgcggagcgg tccgagaggt tcttgatcag ttcggcgacc    10260
tgctggcgga accgggtatc cgtcacgcgg tcatattcgt cgaggatgat cagaacgcgg    10320
gtgccggtga tgtcgcgcca cagatcggcg agttcgcccg aatcgaacga tccggtcggc    10380
aggcgatcgg cgaggcttcc gcccgattcc gcctcgcccg cattgggcga gacgccgcga    10440
tggaacagca gcggcacatc ctctagcacc gcgcggaaca ggtcggcgaa gttggcattg    10500
gcgccgcagg tcgcgtagct gacgatgtag ctggattcac gcgccacgtc ggtcagcaca    10560
tggagcagcg aggtcttgcc gatgccgcgc tcgccataga gcacgacatg gctgcgctgg    10620
ctctcgatcg ccgagatcag ccgcgccagc acctcgaggc gaccggcaaa gctcgagcgg    10680
tccgccaccg gctgggtggg cgtgaagaag gtggcgagcg caaaccgcgc gcgggtgatc    10740
tcgcgacgct cttccggcg ccggtcgagc gggcgatcga gcgcggaagc gcgaaaggtc     10800
ggaaagtcgg gtcgcccgcg gcccgcatgc gcgtcgcgat ggggaacgac ggtggcggcc    10860
agcgggaaat atccgtcctc ctccggtacg tcccgacgcc caagggcca caagaacttc     10920 agcgcggatc ctacagccac tcgaacacct cttaatttcg gacgccgcca cgctcggcag    10980 cgaaccctg gttcgcgcct tctggcgcct ccccaaacg atccggcccc gcctgtatca      11040
gcggcgcttg aaaaactcgt acggtttgat cacgaacgca atgtacgcca gcaccaatac    11100
aatcgtgagg attgcgaaaa catgatagtt ttcgttcccg agataattgg cgacggcaca    11160
tccgaccgcg ggaggcaaat agctgatcat cgtgtcgcgc actaccgaat ccgcctggga    11220
tcgttgcaag aagatcacga tcaggccggc gaatatcgcg atggtcaccc aatcataggg    11280
cgtctgcatg catgtccttt cttttcggcg ccggaatcga aggacttccg acgtcgcccg    11340
aaccgcacta gcagcggacg gtgcaactcg ctagataccg cggtgcagga taaaagctcg    11400
ttaaaacgcg accctaggaa tagcgcggta gcgccggcat gcgagaggtc gggcatgcgg    11460
aaggccgaag cggccgggac agcaccggat gggaggatat tccgtagtg ggagtggcga     11520 ggccatggca tcctcagatc cggttgcttg tactggaggc cattgataat gaagccagga    11580
cccgggggaa cattcgtgcc agtaaaagac gttcagcaag cggtagaagt gcgcctcggc    11640
gatcgtgtct cgcgatcgtg ccgcgtgctc gcgctgcttg cgacggcaac ggcgatccag    11700
cccgcgctcg cgcagcgaca ggcgttcacg ccacgcccga gcggcagcga gcgccagatc    11760
```

```
agcgtgcatg caacgggaca gctcgagtac aacgacaatg tcgtgctcaa cgacccgcgc    11820
atcaccagcg gcgcgcgcgg cgacgtgatc gcctccccct ccctcgatct gagcattgtc    11880
ctgccgcgcg cgaccggaca gctctatctc gcgggcacgg tgggctatcg cttctatcgt    11940
cgctacacga acttcaatcg cgagaatatc tcgctcaccg gcggcggcga ccagcggatc    12000
gcgtcctgcg tggtgcatgg cgaagtcggc tatcagcgcc acctgacgga cctgtccagc    12060
gtcctcgtcc aggatactgc gcccgcgctc aacaacacgg aagaagcgcg cgcctattcc    12120
gcggacatcg gctgcgggtc cgcctacggc ctgcgccctg cacttgccta ttcgcgcaac    12180
gaggttcgca acagcctcgc ccagcgcaag ttcgccgatt ccgacaccaa cacggtcact    12240
gcccagttgg gcctgacgtc gccggcgctg ggcaccgtgt cggtgtttgg acgcatgtcc    12300
gacagcagct acatccatcg cacggtaccg ggggtcagtg gccgcgacgg catgaagagc    12360
tatgcggccg gcgtccagct cgagcgggcg gtctccagcc ggctgaattt ccgcggctcc    12420
gtcaattatt cggaggtcga ccccaagctc gcctcgacgc cgggcttcag cgggatcgga    12480
ttcgatctgt cggcggtata ttcgggcgat caatatggcg tgcagctcct tgcgtcgcgc    12540
aacccgcagc cctccacgct gctgttcgta ggctatgaaa ttgtgacgac cgtgtcggca    12600
acggcaaccc gtaagctgag cgatcggacc caactctcgc tacaggccac caagacctgg    12660
cgcgagcttg cctcttcgcg gttgttcact cttgcgccga cgacgggcaa cgacaacacg    12720
ctgacgctgt tcggcaccgt gaacttccga cccaatcctc ggctgaactt ctcgctgggt    12780
gcgggctata acaagcgcac cagcaatatt gggctgtatc aataccgctc caaacgtatc    12840
aatctcacga cgtcgctgtc gctctgacaa gggccgtatt catgcatgac aaacaccgtt    12900
tcgtgatcct ttcggcgctc accggaattg ccgtactcgc cgcgcccgcg gcagcgcaga    12960
ttcccacccg gtccgttccg acgccggcgc gggcgcgccc ggcgacccccg ccagcggccc    13020 cgcagcagca gacgacggca gtgccgacaa cggcagccac cgccacccccg ccggctgcgg    13080 gtgcggcgcc ggccggctac aagatcggcg tcgacgacgt gatcgaggcg gacgttctgg    13140
gccagtcgga cttcaagacc cgcgcgcgcg tgcaagcgga cggtaccgtc acccttccct    13200
atctcggcgc cgtgcaggta cggggcgaga ccgccgtcac gctggccgag aagctcgccg    13260
gcctgctgcg cgcgggtggc tattacgcga agccgatcgt cagcgtcgaa gtcgtcagct    13320
tcgtcagcaa ctatgtgacg gtgctgggcc aggtgaccac ggccggcctg cagccggtgg    13380
atcgcggcta tcacgtctcg gagatcatcg cgcgcgccgg cggccttcgc gccgatgcgg    13440
ccgatttcgt ggtgctcacc cgcgccgacg gcaccagtgc caagctgaac tacaagcagc    13500
tggcccaggg cggcccggag caggatccgg tggtcacgcc tggcgacaag ctgttcgtgc    13560
cggaagtcga gcacttctac atttatggcc aagttaacgc gcctggggta tacgcgattc    13620
gaacggacat gacgctccgt cgcgcgctgg cacaaggcgg cggccttacc cccgccggct    13680
cgtcgaagcg agtgaaggtc tcgcgcgacg gccaggaaat caagttgaag atggacgatc    13740
cgatcaagcc tggcgacacg atcgtcatcg gcgagcggtt gttctgatct aggcaatgtt    13800
gacagcggac gaggcccacc agtgaatatc attcagttct tccgcattct ctgggtgcgc    13860
cggtggatca tcctcccggc gtttctcgtc tgcgtcacca ccgcggcgct ggtggtccag    13920
ttcctgcccg aacgctaccg cgcgaccacg cggctggtgc tcgacaccct caagcccgat    13980
cccgtcaccg gccaggtgat gaactcgcag ttcatgcgcg cctatgtcca gacgcagacc    14040
gagctgatcg aggactatgc gacctccggc cgcgtggtcg acgaactggg ctgggccaac    14100
```

-continued

```
gatcctgcca acatcgctgc cttcaacgcc tcgtcctcgg cggcgaccgg cgacattcgc    14160
cgctggctcg caaagcagat ctcggacaac accaaggcgg atgtgatcga gggcagcaac    14220
atcctcgaaa tctcctactc ggacagctcg cccgagcgtg ccgagcgtat cgccaacctg    14280
atccgcaccg cattcctcgc ccagtcgctc gccgccaagc gccaggcggc ggcgaagtcg    14340
gccgactggt acacccagca agcggaagcg gcacgccagt cgctgctcgc ggcggtgcag    14400
gcgcgcaccg acttcgtgaa gaagtccggc atcgtgctga ccgagaccgg ttcggatctc    14460
gatacgcaga agctcgcaca gctccagggc gcgagcgcga taccgtcggc accggtcgtc    14520
gcggccgcca gcggcatggg cccggcgcag ctccagcttg cccagatcga ccagcagatc    14580
cagcaggcgg ccaccaatct cggcccgaac caccccggcct tccaggccct gcagcgccag    14640
cgcgaggtgc tcgcccgcgc agcggcggcg gaacgcagcc aggcaagcgc cagcggcccc    14700
ggccgcggcg cgctggaaag cgaagccaat gcccagcgcg cccgcgtgct cggcaaccgc    14760
caggatgtcg acaaggtcat gcagctccag cgggacgtca cgctgaagca ggaccagtat    14820
atgaaggcgg cccagcgcgt cgccgatctg cgcctggaag caagcagcaa cgacacgggc    14880
atgagcacgc tgagcgaagc cagcgcgccg gaaacgccct attccccaa ggtgccgatg    14940 atcatcggcg gcgcggccgg cttcggcctc ggcctcggcg tgctggtcgc gctgctcgtc    15000
gaactgctcg gtcgccgcgt gcgcagcgcc gaggatctcg aagtggcggt cgatgcgccg    15060
gtgctgggcg tgatccagag ccgtgcctcg ctcgccgcac gcctgcgccg cgcccaagaa    15120
accctcggcg accgcgccga aacgcacgga gcttcagtaa actgatggac gcgatgacca    15180
gcgaaccgct gcccgaaggc gagcgcccga gcgccgttcc gacgacgccc gacaccaccg    15240
gcgtcctgga atatcagctc gtcctgtccg acccgaacgg catcgaagcg gaagccattc    15300
gcgcgctgcg caccgcatc atggcgcagc acctgcgcga gggccgccgc gccctggcga    15360
tctgcggcgc ctcggccggc gtcggctgca gcttcaccgc cgccaacctc gcgacggcgc    15420
tggcgcagat cggcatcaag accgcgctgg tcgatgccaa tctgcgcgac ccgagcatcg    15480
gcagcgcctt caacatcgcc gccgacaagc cgggcctcgc cgactatctc gcctcgggcg    15540
atatcgacct cgcctcgatc atccaccga ccaagctgga ccagctgtcg gtgatccatg    15600
ccgggcatgt cgagcacagc ccgcaggaac tgctgtcctc cgagcagttc cacgacctcg    15660
tgacgcagct gctgcgcgag ttcgacatca cgatcttcga caccacggcc gcgaacacct    15720
gcgccgatgc gcagcgcgtc gcacatgtcg ccggctatgc gatcatcgtg gggcggaagg    15780
attcgagcta catccgcgac gtcaacacgc tcacccgcac gctgcggtcg gaccgcacca    15840
acgtcatcgg ctgcgtcctg aacggctatt gaattggatt ccatgaccgc gactgcgctg    15900
gagcggcagc aaggacggcg acagggggc tattggctcg cggtcgccgg ccttgcggca    15960
ctcgccattc ccactttcgt cacgctcggc cgcgaaacct ggagcgccga aggtggcgtg    16020
caggggccga tcgtgctggc gaccggcgcc tggatgctgg cgcggcaacg cgacagcctc    16080
gtggcgctcc ggcgccccgg caatctggcg ctgggcgcat tgtgcctgtt gctggcgctg    16140
ggcatctaca ccgtcggtcg cgtgttcgac ttcatcagca tcgagacgtt cgggctggtc    16200
gcgaccttcg tggcggctgc gttcctctat ttcggcggcc gggcgctgcg cgctgcgtgg    16260
ttcccgacct tgtggctgtt cttcctcgtg ccgccgccgg gctggatcgt cgatcgcgtc    16320
accgcgccgc tcaaggagtt cgtctcctat gccgccaccg gcttcctgtc ctggctggac    16380
tatccgatcc tgcgccaggg cgtgacgctg ttcgtcggcc cctatcagct gctggtcgag    16440
gatgcctgtt cggggctgcg ctcgctctcc agcctcgtcg tcgtcacgct gctgtacatc    16500
```

```
tacatcaaga acaagccgtc ctggcgctac gcgctgttca tcgccgcgct ggtgatcccg   16560
gtcgcggtga tcaccaacat cctgcgcatc gtcatcctcg tgctgatcac ctatcatatg   16620
ggcgacgagg ccgcgcagag cttcctccac gtctccaccg gcatggtgat gttcgtggtc   16680
gcgctgctct gcatcttcgc catcgactgg gtggtcgaac agctcttcac acggcgccgg   16740
aggccccatg ttcaaccggc gtgacctgct gatcggcgcg ggctgcttcg ccgccgccgg   16800
cgcctcgctc ggcctcaagc cgcaccgtcg catggacctg ctcggtgcga ccaagctcga   16860
tgcgctgatg cccaaggcat tggcggctg gaaggccgag gataccggtg cgctgatcgc   16920
ccccgcgcgc gaaggcagcc tggaagacaa gctgtacaac caggtggtcg cccgtgcctt   16980
ttcgcgcgcc gacggcaccc aggtgatgct gctgatcgcc tatggcaacg cccagacgga   17040
tctgctgcag ctccaccgac cggaagtctg ctacccgttc ttcggcttca ccgtggtcga   17100
gagccacgag cagatcatcc cggtgacgcc gcaggtgacg attcccggac gggcgctgac   17160
cgcgaccaac ttcaaccgca ccgagcagat cctctactgg acccgcgtgg gcgaatatct   17220
gccgcagaac ggcaacgagc agctgttcgc ccgcctcaag agccagctcc agggctggat   17280
cgtcgacggg gtgctggtcc gcatctcgac tgtgacggcg gaagccaagg acggcctcaa   17340
cgccaatctc gatttcgcgc gcgagctggt gaagacgctc gatccgcgcg tgctgcgccc   17400
gttgctcggc acgcaggtaa cgcgcgacct ggcgccgcgc gcctgaacga aaaaggggcg   17460
gcgcagaccg ccgcccctcc ctctccttct cgtcgcgtac ccgcgctcag cgctcgtgca   17520
gcgcgtcgct gccggtttcg agcatcgggc cgacgagata gctcagcaat gtccgcttgc   17580
cggtgacgat gtcggcactg gcgatcatgc ccggccgcag cggcacgtgc ccgccattgg   17640
cgatgacata gccgcggtcc agtgcgatcc gcgccttgta gaccggcggc tggccctcct   17700
tcacctgcac cgcctcgggc gcgatgccca ccaccgtgcc ggggatcatg ccatagcggg   17760
tgtgcgggaa cgcctgcagc ttcaccttta ccggcatgcc ggtgcgcacg aagccgatat   17820
cgctgttgtc caccatcacc tcggcctcga gccgggcatt gtccggcacc agcgacagca   17880
gcggcttggc gccctccacc acgccgcctt cggtgtggac ctgcagctgc gagaccgtgc   17940
cgctgaccgg cgcgcgcagt tcgcggaacg aactgcgcag attcgccttg gcgacttcct   18000
cgctgcgcgc ccgcacgtcg tcctgcgcct tcaccagatc ctgcaacacc tgcgcgcgcg   18060
cctcctcgcg cgtcctgatc gacatgctgc tggcactgcg cgactgctga ccaagcttgg   18120
ccaccgtcgc ccgcgccgcg gtgaggtcct gccgttcgga aatgagctgg cggcgcatct   18180
cgaccacgcg cagcttcgag acatagccct tggcggccat cgcctcgttc gcggcgatct   18240
gctgctcgag cagcggcagc gattgttcca gcttgcgaac ctgcgcctgt gcctcggccg   18300
aggcggaagc ggcggcaccg ctgtccgatc ggccgccggc aagcatcgcc tcgatctggc   18360
cgagccgcgc cgtgcgagg ccgcgatgcg tctcgacctc cgcggcgcct gcggcggcgg   18420
gcgcggcgaa gcggaagccc tttccgtcca gcgcgtcgat gatcgcctgg ttgcgcgcgg   18480
catcgagctg ggcgctgagc agcgccacgc gcgcctgcgc ggcttcggct gccgacatgg   18540
tgggatcgag cgtgatcagc acctggccct tctgaacctt ctgcccctcg cccaccagaa   18600
tgcgccggac gataccgctt tcgggggact gcacgatctt ggtctcgccg atcgggcga   18660 tgcggccctg cgtcggcgcc accacttcca cgcggccgat tgccagccag cggtggtga   18720 tcgccagccc cgccaccatc acccggccgg tgaggcgcgc ggtgggcgac accggacgtt   18780
cgatgatctc gagcgcggcc ggcaggaatt cggtatcata ggcatcggcg cgagcgggca   18840
```

-continued

```
gcacggtgcc gcgcatgcgg gcgatcgggc cgccgcggcc gatcggaaca acggcgttca    18900
tgcggcaatc tccccatatc cgctttggcg gcggtgcagg tcggcatagc ggccgcccaa    18960
gcgtagcagt tcgtcatgcc ggccgctctc gacgatgcgg ccctgctcca gcgtgatgat    19020
ccgatcgcag gcgcgtaccg cggacaggcg gtgggcgatg atcaccagcg tgcggcccgc    19080
cgagatggcg cgcagattgt tctggatcag ctcctcgctc tcggcatcca gcgcggaggt    19140
cgcctcgtcg aacaccagga tgcgcggatt gccgaccagc gcgcgggcga tagcgagccg    19200
ctggcgctgg ccgcccgaca ggttgacgcc gcgctcgacg atctcggtgt catagccgcg    19260
cggctgacgc aggatgaagt catgcgcacc cgccagcgtc gccgccgcca cgacatgctc    19320
gaacggcatc gccgggttgg acagcgcaat gttctcgcgg atcgagcggc tgaacagcag    19380
attttcctgc agcacgacgc cgatctgccg gcgcagccag gcgggatcga gctgggccac    19440
atccacctcg tcgaccagca cgcggcccag atcgggggtg ttgaggcgct gcagcagctt    19500
ggccagcgtc gacttgcccg accccgagga gccgacgatg ccgagcgacg tgccggcggg    19560
gatgtcgagc gtgatgtcgc tcagcaccgg cggctggtcc tcggcatagc ggaaggtcac    19620
gttttcgaag cggatcgcgc cgcgcagcac cggcagcgtc gcggcggagg ccggccgcgg    19680
ctccaccgga tggttgagca cgtcgccgag gcgctcgatc gcgatgcgga cctgctggaa    19740
gtcctgccac agctgggcca tgcggatcac ggggccggaa acgcgctggg cgaacatgtt    19800
gaacgccacg agcgcgccga cgctcatcgc gccaccgatc acggccttgg cgccgaagaa    19860
caggatcgcc gcgaagctca gcttggagat cagctcgatc gcctggctgc cggtgttggc    19920
gacgttgatc agccgctgcg acgaggcggt ataggcggcg agctgacgtt cccagcgatt    19980
ctgccagtgc ggttcgactg cggtcgcctt gatggtgtgg atgccggaga cgctctcgac    20040
gagcagcgcg ttgctggcgg agctcttctc gaacttgtcc tcgacacgcg tgcgcagcgg    20100
gcccgcgacg ccgaacgaga ccatcgcata ggcgaccagc gacacgatca cgacgccgaa    20160
cagcatcggc gagtagaaca gcatcgcgcc gaggaacacg accgtgaaca gcggatcgac    20220
catcaccgtc agcgacgcat tggtgaggaa ttcccggatg gtctcgagct ggcggacccg    20280
ggtgacggtg tcgcccaccc gccgcttttc gaaatagccg agcggcagcg ccagcagatg    20340
gtggaacagc cgcgcgccca gctcgacgtc gatcttctgc gtcgtctcgg tgaacaggcg    20400
cgtgcggatc cagcccagcg ccacctccca gaccgacacg gccaggaagg cgaaggcgag    20460
cacgctcagc gtgctcatgc tgttgtggac cagcaccttg tcgatcacgc tctgaagag    20520 cagcggcgcc gcgaggccga gcaggttgag cgccagggtg atgcccagca cctcgagaaa    20580
cagcctgcga taccgctgga actgtgcggc gaaccaggag aaaccgaatc gcagcgcctg    20640
gccggccacg gcgcgcgtcg tcagcagcac gagcgtgccg gaccacagcg catccagccc    20700
ctcgcggtcg acctgttcgg gggcgtggcc gggacgctgg atgatcacgc catgctcggt    20760
caggccaccg atcacgaacc agccctccgg gccgtcggcg atggccggca gcggctggcg    20820
ggccagaccg ccgcgcggca cgtccaccgc cttggcgcgc acgccctgct ggcgcttggc    20880
gagcaggatc aggtcgtcga cgctggcacc ctcggcatgg cccagcatgt gccgcagctg    20940
ttcgggggtg acgcgatgt tgtggacgcc gagcagcagc gacagcgcca caagcccgga    21000
ttcgcgcaat tcgccctcgc gctcggcggc agcctgggcg gcgaacgcgc cctggagctg    21060
tgcctgcatc tcgtcgcgtg tcattccggt actctgcctc catggcgcta ctgatcgcag    21120
ccatgatgaa cgagctcggt aaagactcgc ttaagccaga ttttttctgtg gtttataacct   21180 attgccgggg atgccggacc ggaccggatc ggcagacggc agcctgcgtt agtcgggcct    21240
```

```
taaagcgttg ccgctagcac aaggacaaga attttatcgg agagggtcgg gaaccatgcc   21300
cacgcatgaa ggttgcagcg cagcaatatc gacggatcgc ctcggagccc gaatgctgca   21360
tccgcgaagt gactttcgcc aaagcagcta taggatggcc cggggcttga ttgccgccgt   21420
gcgatcagca taagcgatcc atggtcgcca aaatctgtca tccttggtaa caatcatgca   21480
gccgctaagg aagatgtgca cgtctgacga tgctttcttc cgcaccccat gcgccgctga   21540
ctctggtaga ttgaccgtgg cctccattgc tcatcgtctc gaaaaaggac cctctggtcg   21600
ccgcgcggac ttccgggaat cgatttgtcc cgttatagtg caatgcaaca ggccgaatcg   21660
gccgctgtca gcgtgcacaa tccgttgagg gagcccgacg aggcaatgaa cgcttttgaa   21720
gcacagcgcg cctttgagga gcagctccgg gcccatgccc gttctgcccc cagcgccgca   21780
cccatgctgc gacgttccac gatccgcatg atcctctaca ccgaattgct gttgctcgac   21840
agcatcgcaa ttctactggg gttctacatc gcggcctgct cgcgcgacgg caactggctg   21900
tcccttgcgg gcgtcaatgt cggcatcttc ctcctgccga tcacgctcgg caccgcgctc   21960
gccagcggca cctattcgct gagctgcctg cgctacccgg tcagcggggt gaagagcatc   22020
ttctcggcgt tcttcttctc ggtgttcatc gtgctgctgg gcagctacct gctcaccgcg   22080
gagctgccgc tgtcgcgcct gcagctcggc gagggcgtgc tcctggcgct cagcctggtg   22140
acgatctgcc gccttggctt ccgctggcac gttcgtgcgc tgacacgcgg cacgctgctc   22200
gacgagctgg tgatcgtcga cggcgttgcc ctggaggtcg cgagcggcgc ggtcgcgctc   22260
gatgcgcgca tcatcaacct cacgcccaac ccgcgcgatc cgcagatgct gcatcgcctc   22320
ggcaccaccg tggtgggctt cgaccgggtc gtcgtcgcct gcaccgagga gcaccgggca   22380
gtatgggcgc tgctgctcaa gggcatgaac atcaagggcg agatcctcgt cccccagttc   22440
aacgcgctgg gcgcgatcgg cgtcgactcc tatgagggca aggacacgct ggtcgtgtcc   22500
cagggcccgc tcaacatgcc gaaccgcgca aagaagcggg cgctcgatct gctcatcacc   22560
gtccccgcgc tggtcgcgct ggcgccgctg atgatcgtgg tcgcgatcct gatcaagctg   22620
gagagccccg gccccgtctt cttcgcacag gaccgcgtcg gccgcggcaa ccgactgttc   22680
aagatcctca gttccgctc gatgcgcgtt gcgctctgcg atgcgaacgg caacgtctcg   22740
gccagccgcg atgacgatcg catcaccaag gtaggccgga tcatccgcaa gaccagcatc   22800
gacgagctgc cgcagctgct caacgtgctg cgcggcgaca tgagcgtcgt cggcccgcgc   22860
ccgcacgcac tcgggtcgcg cgccgccaac catctcttct gggaaatcga cgagcgctac   22920
tggcaccgcc acacgctcaa gccgggcatg acgggcctcg cgcagatccg cggcttccgc   22980
ggcgcgaccg atcgccgcgt cgatctcacc aatcgcctgc aggcggacat ggagtatatc   23040
gacggctggg acatctggcg ggacgtcacc atcctgttca agacgctgcg cgtgatcgtg   23100
cactccaacg ccttctgatc gcggagggga gcaacgcgag caccgcttgg tgcaagagca   23160
ttgacatccg ccctgcttct gcatttgtca ttttatcatt gtcgttgcgg gccgcccgc   23220 gccatggggg attttgaatg aagggtatca tccttgcggg gggcagcggc acgcgcctct   23280
accccgcaac gctgtcgatc tcgaagcagc tgcttcccgt ctatgacaag ccgatgatct   23340
tctaccccct gtcggtgctg atgctcacgg gtatccggga catcctgatc atctccaccc   23400
cgcgcgacct gccgatgttc caggcgctgc tcggcgacgg ttcggcattc ggcatcaacc   23460
tgagctatgc cgaacagcct tcgcccaacg gccttgcgga agccttcatc atcggcgccg   23520
atttcgtcgg caacgatccc agcgcgctga tcctcggcga caacatctat cacggtgaaa   23580
```

-continued

```
agatgggcga gcgctgccag gcagctgcgg cccaggcatc gcagggcggc gcgaacgtgt    23640
tcgcctatca tgtcgacgat cccgagcgct acggcgtggt cgcgttcgat ccggagacgg    23700
gcgtcgctac cagcgtcgag gaaaagccgg ccaaccccaa gtccaattgg gcgatcaccg    23760
ggctttattt ctacgacaag gacgtggtcg acatcgccaa gtcgatccag ccctcggcgc    23820
gcggcgaact cgagatcacc gacgtcaacc gcatctacat ggagcgcggc gacctccaca    23880
tcacccggct cggtcgcggc tatgcctggc tcgacaccgg cacgcatgac agcctgcacg    23940
aggccggctc gttcgtccgc acgctggagc accgcaccgg cgtgaagatc gcctgcccgg    24000
aggaaatcgc cttcgagagc ggctggctgg gcgccgacga tctgctcaag cgcgccgccg    24060
gcctcggcaa gacggggtat gccgcctatc tgcgcaagct ggtagccgcg gcatgaccca    24120
ggtgcatcac cacgcgctat cgggcgtcat cgagttcacc ccgcccaagt acggcgatca    24180
ccgcggcttc ttctccgagg tgttcaagca gtccacgctc gacgccgaag gcgtcgaggc    24240
gcggtgggtg caggacaatc agagcttctc ggccgcaccg ggcacgatcc gcggactgca    24300
cctgcaggcg ccgcccttcg cccaggccaa gctggtgcgc gtgctgcgcg gcgcgatcta    24360
cgacgtcgcg gtcgacattc gccgcggctc gcccacatac ggccagtggg tcggcgtcga    24420
gctttcggcg gacaagtgga accagctgct ggtgccggcc ggctatgcgc atggcttcat    24480
gacgctcgtc ccggattgcg agatcctcta caaggtcagc gccaaatatt cgaaggaatc    24540
ggagatggcg atccgctggg atgatcccga tctcgccatc acctggccgg acatcggcgt    24600
cgagccggtg ctctccgaaa aggacgcggt cgctaccccg ttcgccgaat caacacccc    24660 cttcttctat cagggctgat ccatgcagca gaccttcctc gttaccggcg gcgccggctt    24720
catcggctcg gcagtggtac gccacctcgt tcgccagggc gcgcgcgtca tcaatctcga    24780
caagctcacc tatgcgggca acccggcctc gctgaccgcg atcgagaacg ccccaacta    24840 ccgcttcgtc cacgccgata tcgccgacac cgcgacgatc ctgccgctgc tgcgcgaaga    24900
gcaggtcgac gtggtgatgc acctcgccgc cgagagccat gtcgatcgct cgatcgacgg    24960
cccgggcgag ttcatcgaga ccaacgtcgt cggcaccttc aagctgctcc aggcggcgct    25020
gcaatattgg cgcgagctgg aaggggagaa gcgcgaggct ttccgcttcc accacatttc    25080
caccgacgag gtgttcggcg acctgccgtt cgacagcggc atcttcaccg aagagacgcc    25140
ctatgatccc tcctcgccct attcggcgtc gaaggcggcc agcgaccatc tggtccgcgc    25200
ctggggtcac acctatggcc tgcccgtggt gctgtcgaac tgctcgaaca attacgggcc    25260
gttccacttc cccgagaagc tgatcccgct gaccatcctc aacgcgctgg aaggcaagcc    25320
cctgcccgtc tacggcaagg gcgagaatat ccgcgactgg ctgtacgtcg acatcacgc    25380 caaggcgctg gcgacgatcg ccacgaccgg caaggtcggc cagagctaca atgtcggcgg    25440
ccgcaacgag cgcaccaacc tgcaggtcgt cgagacgatc tgcgacctgc tcgatcagcg    25500
cattccgctg aaggatggca agaagcgccg cgagctgatc accttcgtca ccgatcgccc    25560
cggccatgac cgccgctacg cgatcgacgc gaccaagctc gagaccgaac tgggctggaa    25620
ggccgaggag aatttcgaca ccggcatcgc cgcgacgatc gactggtatc tcgagaatga    25680
atggtggtgg ggtccgatcc gctccggcaa atatgccggc gagcggttgg ggcagaccgc    25740
ctgatgcgca tcctcgtcac cggcatgac ggccaggtcg cccaggcgct gggcgaacag    25800
gcggagggcc atgagctgat cttcaccagc tatcccgagt tcgatctctc caagccggag    25860
acgatcgagg cggcggtggc gaaatccag cccgagctga tcgtgtcggc ggctgcgtat    25920
acggcggtcg acaagtccga gagcgagccc gagctcgcca tggcgatcaa cggcgacggc    25980
```

```
cccggcgtac tggcgcgcgc gggcgcgaag atcggcgcgc cgatcatcca tctgtcgacc   26040
gactatgtgt tcgacggcag cctggaccgc ccgtggcgcg aagacgaccc caccggtccg   26100
ctcggcgtct atggcgccac caagctggcc ggcgagcaag cggtgcaggc ctcggcgcg    26160 accaacgcgg tgatccggct cgcctgggtc tacagcccgt tcggcaacaa cttcgtcaag   26220
acgatgctgc gcctcgccga gacgcgggac acgctgaacg tggtcgagga ccagcagggc   26280
tgcccgagct cggcgctgga catcgccacg gcgatcctca aggtcgtcgg ccactggcag   26340
cagaacggcg ccaccagcgg cctgtatcac ttcaccggat cgggcgagac caactgggcc   26400
gacttcgcgc gcgcgatctt cgcggaaagc gccaagcacg gcggtccgac cgccgaggtg   26460
accggcattc cgacctccgg ctaccccacc ccggcgaagc gcccgccaa ttcgcggctc    26520 aattgcgaca agttcgccga aaccttcggc tatcgtgcac ccgcctggca ggactcggtg   26580
gcggaagtgg taggccgcct cctggcataa aatgcccggc ccgaccctgt gcgcggcggg   26640
gtggctgcgc actccggtcg ggtttcatcg acatcgccgg ctgcggggag catcaccgat   26700
gctccccgat cagcgccagg ccgtcacttc ctgaacggcg cgaccagggg cttgatcgtc   26760
ttgaacacgg cctcacgcag cgtccgcacg ggcgcggcga cgaggtgatc gaacgcgagc   26820
gtcatcccgc tcacccgctg gggtgcgacg tcgctgcgga tcttgaacga ttcgaccacc   26880
tcgatatcgg aaaccagccg ccccttgatg cggttgatga cattctcgcc atgcaccacc   26940
tgcagccata ccgccgcccc ggcgacctgg gtgatcttcc acttctggcc cagctcatga   27000
tggggcttgg cccagatcgt ctcgacgctg gcgagatcgc gctcgaccag cgaggtgaac   27060
ggattgctgt ggtccgcagc ggtgtagagc cggccctggc gcatcgcgat gccctgggtg   27120
aagttcagca ccgtctgtgc cggcgcatcc ttcgccgcgg cctgcacccg tgccacgaag   27180
tcgttcgaaa gcgcgtcgtc attgtccagc cgcgtggtga cgatcagctg ctcgccgggc   27240
gtcgccagcg ccttcacgtc gtccgcgatc atcgccttgt cgaacatcgc gacgtagcgc   27300
ggcgtgaagt tgtagatctg ccgatcgcgc tcgatccgct cgcggaactc ggcggggtg    27360 tccttgtcga agtagatgag ccagtggaag ttgcgctcgg tctggcccgc gatgctcggc   27420
aggcagaact gctcgaacag cccgaaacgg cggtcgagcc aacccggcga attgcggatc   27480
gccacctcgc ggcccgggct ggcgatgttg aagcgcgtca ggatcacgtg aagcatcggt   27540
tcgatcagcc ccggtctagc aaaacgaaga aagcccggcc gctacaacgg ccttgttcga   27600
acaacgcgca agaaacaggg tacacgcgaa cggcacgttc gtcttcgccc accccgctgg   27660
ttgccgccat tcccacgaac ggttacggga tattccggaa ctgggcaacc ggggattgct   27720
gcactgcgca atgacacgcg gccggaatga caaacggctt gccgcccgcg ccccccgcgc   27780
ctaaccctcc gcccgtgccc gacgcccgtc ccgatcgcat tgccaccggc ctggcgcttc   27840
gcctgttcgc cattgcctgc ctgtcgacca tgtcggcgct catcaagatg tcggaactgc   27900
gcggcgcctc gctgatcgag acgatgttcc accgccagct ctgggcggtg ccgctggtca   27960
ccttgtgggt ggtgatgggc ccggggctca agtcgctcaa gacgcagcgc ttcggcgcgc   28020
atgtctggcg caccgcggtg ggcctcaccg gcatgatctt caccttcggc gcggtgatcc   28080
tgctgcccct ggccgaggcg cagaccttcc agttcaccgt gccatcttc gccacgctgc    28140 tcggcgcgct gatcctcggc gagccgaccg gccggcatcg ctgggcgca gtgatcgtcg    28200 gcttcctcgg cgtgctgatc gtcgtccagc cgggccggga agccattccg atcttcggcg   28260
ccttcgtcgg gctgatggcg gcgttgttcg tcgccatcgt cgcgatcacg ctgcggcaga   28320
```

-continued

```
tcacccgcac cgaaagcgcc ggcaccaccg tcttctggtt ctcgctgctc tcggtgcccg  28380
tgctcggcgc catctacgcg ttcaacttcc gtccgcacga tgccgagacc tgggcgatcc  28440
tcatcgccac aggactggtg ggcggcgtcg gccagctggc gctgaccggt gcgatgcgct  28500
tcgcccccgt ctcggcggtg gtaccgatgg actattcggg gctgatctgg gcgacgctct  28560
acggctggct gctgttcgac gtgttcccga ccttctcgac ctggctcggt gcgccggtga  28620
tcatcgccag cgggctctac atcgtctatc gcgagcagaa gctggcccgc ggccaggcta  28680
gctacgccga aacgccacta tgaggttgtt ggcgggcatc gccacccgcc gatcgaacac  28740
caggccttgc gcccccgccg ccgcgatcac ctcgtccagc aagcgcagcc cccaggcagg  28800
atcc                                                               28804
```

PRODUCTION OF NON-NATIVE BACTERIAL EXOPOLYSACCHARIDE IN A RECOMBINANT BACTERIAL HOST

CROSS-REFERENCE TO RELATED APPLICATIONS

The present application is a continuation-in-part of copending application Ser. No. 09/096,867, filed Jun. 11, 1998, and claims the priority of provisional application Ser. No. 60/049,428, filed Jun. 12, 1997. The contents of both applications are incorporated herein by reference.

BACKGROUND OF THE INVENTION

Xanthan gum is an acidic exopolysaccharide (EPS) normally secreted by *X. campestris* (Jeanes, A., et al., 1961, J Appl Polymer Sci 5: 519–526), and is useful as an aqueous rheological control agent because it exhibits high viscosity at low concentration, pseudoplasticity, and insensitivity to a wide range of temperature, pH, and electrolyte conditions (see U.S. Pat. Nos. 5,194,386, 5,472,870, 5,279,961, 5,338,841, and 5,340,743, the contents of each of which are incorporated herein by reference). The genes that code for its synthesis are gumB through M(Capage, M. A., et al., 1987, WO87/05938; Vanderslice, R. W., et al., 1989, the contents of which are incorporated by reference; Genetic engineering of polysaccharide structure in *Xanthomonas campestris*. In: Biomedical and biotechnological advances in industrial polysaccharides, V. Crescenzi, I. C. M. Dea, S. Paoletti, S. S. Stivala, and I. W. Sutherland, eds, pp 145–156, Gordon and Breach Science Publishers, New York).

A different source of commercially significant and functionally diverse biopolymers is the genus Sphingomonas (Pollock, T. J., 1993, J Gen Microbiol 139: 1939–1945). Different organisms of this genus secrete a variety of different strain-specific exopolysaccharides For example, one species secretes Gellan®, while others secrete welan, rhamsan, S-88 or other polysaccharides (Moorhouse, R., 1987, Structure/property relationships of a family of microbial polysaccharides. In: Industrial polysaccharides: genetic engineering, structure/property relations and applications. M Yalpani, ed, pp 187–206, Elsevier Science Publishers B.V. Amsterdam).

We refer to this group of polymers as "sphingans," after the common genus, because they also have common carbohydrate backbone structures (-x-glucose-glucuronic acid-glucose-; where x is either L-rhamnose or L-mannose) with distinct side chains. (See U.S. patent application Ser. Nos. 08/592,874, filed Jan. 24, 1996, and 08/377,440, filed Jan. 24, 1995, the contents of each of which are hereby incorporated by reference). The structure for sphingan S-88 is shown in FIG. 1. The organization and DNA sequence of 23 genes (FIG. 2) that direct the synthesis of sphingan S-88 have been described (Yamazaki, M, et al., 1996, J Bacteriol 178: 2676–2687).

The commercial production of highly viscous xanthan gum and other bacterial polysaccharides is a complex biosynthetic and process-engineering problem (Kennedy, J. F. et al., 1984, Prog Industrial Microbiol 19: 319–371). The sugar substrate is important primarily because the sugar affects productivity, but the cost of the sugar can also be significant. Currently, xanthan gum is produced by supplying X campestris with corn syrup, sucrose or starch. Yet, three to four typical cheese factories can provide enough low-value lactose-containing waste whey to satisfy all of the existing worldwide demand for xanthan production.

A recombinant strain that can stably convert lactose into xanthan gum in amounts equal to the conversion of glucose is disclosed in U.S. Pat. Nos. 5,434,078, and 5,279,961, the contents of each of which are incorporated herein by reference.

It is desired to improve the methods of the production of xanthan gum to achieve more cost-effectiveness, convenience, more desired product qualities and greater production efficiency.

A problem encountered with xanthan gum produced by conventional methods, is that it is contaminated with a cellulase which can be very disadvantageous in commercial applications where xanthan is mixed with or contacts cellulosic polymers. The result is deterioration of the cellulosic polymers.

Methods are known for the treatment of xanthan gum which has been separated from fermentation broths to remove the cellulase contaminant. However, these treatments require processing of the xanthan gum and add to the expense and overall complexity of the process.

SUMMARY OF THE INVENTION

Figure 1:
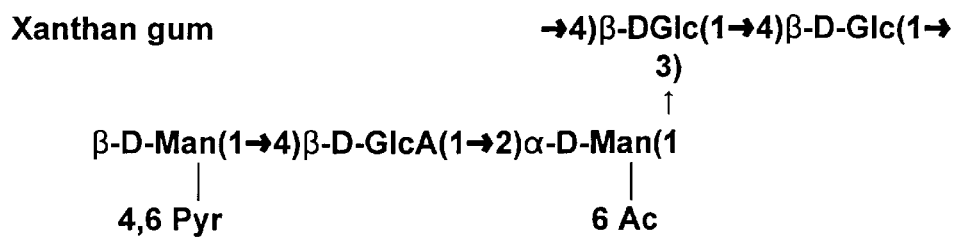
FIG. 1 shows the repeating subunit structures of xanthan gum and sphingan S-88.
Figure 1:
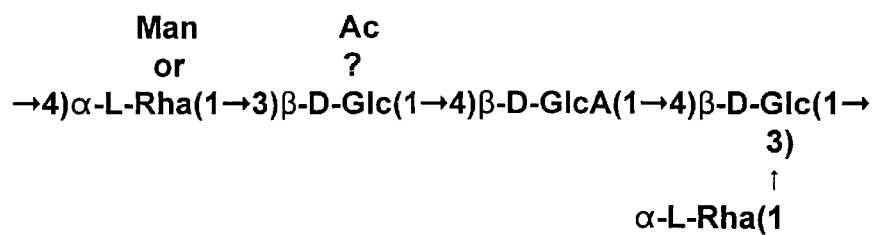
Figure 2:
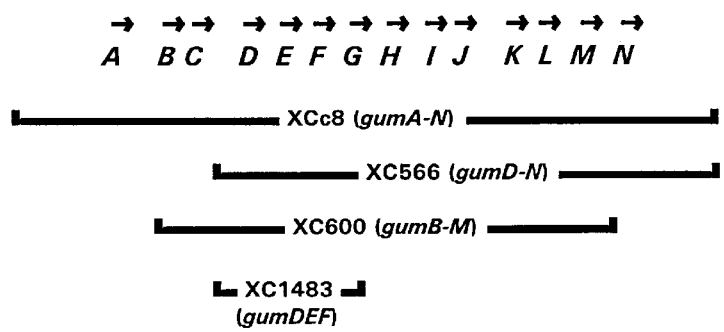
FIG. 2 is a schematic map of the X campestris gum and Sphingomonas S88 sps genes.
Figure 2:
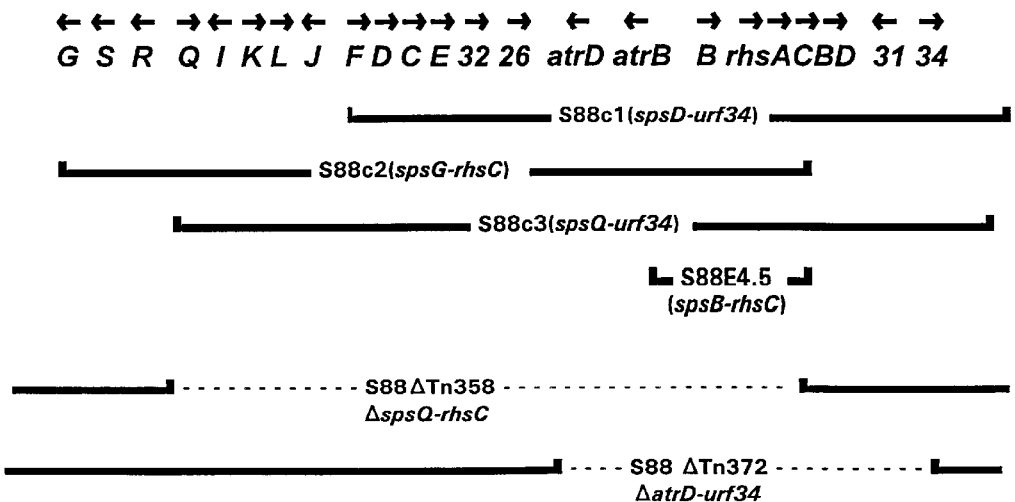

We have discovered new recombinant bacteria for the production of exopolysaccharides. In addition, we have discovered a method for making the recombinant bacteria and making an exopolysaccharide from the bacteria by submerged aerobic fermentation of the bacteria utilizing a sugar substrate. The recombinant bacteria of the present invention are able to produce exopolysaccharides and utilize sugar substrates which are utilizable by the bacteria from which the recombinant bacteria were derived. In addition, the exopolysaccharide obtained from the inventive bacteria exhibit improved, more desirable or different properties from the exopolysaccharide produced by the non-recombinant bacteria from which the recombinant bacteria was derived.

In addition, we have discovered a novel xanthan gum product which as obtained in the broth exhibits reduced cellulase contamination. It is an object of the invention to provide a method of producing bacterial exopolysaccharides by fermentation from sugar substrates that the bacteria which the exopolysaccharides are native to cannot utilize.

It is a further object of the invention to provide a method of increasing the yield of a non-native bacterial exopolysaccharide produced in a recombinant bacterial host.

It is another object of the invention to produce xanthan gum by fermentation from whey waste, a byproduct of cheese production.

Additional objects and advantages of the invention will be set forth in part in the description which follows, and in part will be obvious from the description or may be learned from practice of the invention. The objects and advantages may be realized and attained by means of the methods particularly pointed out in the appended claims.

To achieve the objects and in accordance with the purposes of the present invention, methods for the production of non-native bacterial exopolysaccharides in recombinant bacterial hosts are set forth.

Specifically, we have discovered that the yield of a non-native bacterial exopolysaccharide produced in a recombinant bacterial host can be increased by inactivating the native polysaccharide production in the bacterial host.

DEFINITIONS

As used herein:

"Non-recombinant bacterial host strain" means a bacterial strain which does not contain foreign genetic material.

"Recombinant bacterial host strain" means the non-recombinant bacterial host strain into which foreign genetic material has been introduced and retained. This strain is sometimes referred to herein as the "recipient" or "recipient strain."

"Foreign genetic material" means segments of the genome of a strain of bacteria which are different from those in the recombinant bacterial host strain into which the segment(s) is or is to be introduced.

"Glycosyl transferase" means any one of a group of related enzymes which either catalyze the attachment of a sugar-phosphate molecule to the isoprenyl phosphate carrier involved in exopolysaccharide biosynthesis or the attachment of a sugar to sugars previously attached to the isoprenyl phosphate carrier.

An "sps gene" means one of several genes which are present in the genomes of species of Sphingomonas bacteria or can be isolated from the Sphingomonas bacteria and which are involved in the biosynthesis of a sphingan exopolysaccharide because they code for enzymes that catalyze chemical reactions in the biosynthetic pathway or because they code for proteins or DNA control sites that modulate the amount of sphingan exopolysaccharide present in the bacterial growth medium.

"Non-native exopolysaccharide" means a bacterial exopolysaccharide which is not produced and excreted by a non-recombinant bacterial host strain, but is produced and excreted by a recombinant bacterial host strain obtained from the non-recombinant bacterial host strain.;

"Native bacterial producer" means a non-recombinant bacterial strain which produces the desired bacterial exopolysaccharide.

A "gum gene" means one of several genes which are present in the genomes of species of Xanthomonas bacteria or can be isolated from the Xanthomonas bacterial and which are involved in the biosynthesis of a xanthan exopolysaccharide because they code for enzymes that catalyze chemical reactions in the biosynthetic pathway or because they code for proteins or DNA control sites that modulate the amount of xanthan exopolysaccharide present in the bacterial growth medium.

Examples of two exopolysaccharides, xanthan gum and sphingan S-88 (Jansson, P. E., et al., 1975, Carbohydr Res 45: 275–282, Jansson, P. E., et al., 1986, Carbohydr Res 156: 165–172), are shown by their repeating sugar subunit structures in FIG. 1. The arrows point toward the reducing end of each repeat. For xanthan gum the IP carrier is attached at the reducing end through a phosphodiester linkage to the glucose residue which is lacking the side chain (Ielpi, L., et al., 1993, J Bacteriol 175: 2490–2500). Abbreviations: Glc, glucose; Man, mannose; GlcA, glucuronic acid; Rha, rhamnose; Ac, acetyl ester; and Pyr, acetal-linked pyruvic acid. The position and linkage of the Ac in S-88 is unknown.

DESCRIPTION OF THE PREFERRED EMBODIMENTS

The present invention provides a method of producing a bacterial exopolysaccharide from a sugar source which the native bacterial producer of that exopolysaccharide cannot utilize by transforming a bacterial host strain which can utilize the sugar source but does not produce the exopolysaccharide with genes from the native bacterial producer which are necessary for establishing the production of the exopolysaccharide in the bacterial host strain. The bacterial exopolysaccharide can then be produced by fermenting the recombinant bacterial host with the sugar source. For example, the genes gumBCDEFGHIJKL and M from *X. campestris* strain B1459 were transformed into a specifically mutated Sphingomonas recipient, fermentation of which in the presence of inexpensive waste whey lactose obtained large amounts of secreted xanthan gum which was comparable to that produced by *X. campestris* strain B 1459. For production of xanthan gum lacking acetyl side groups, the gumF and gumG genes of Xanthomonas can be omitted from the foreign genetic material obtained from Xanthomonas. Similarly, for production of xanthan gum lacking pyruvyl side groups, the gumL gene can be omitted.

In the case where the "recombinant bacterial host strain" already expresses a gene function that is necessary for production of the "non-native exopolysaccharide", then that function need not be included in the "foreign genetic material". For example, when foreign genetic material is introduced into Sphingomonas bacteria and the initial step in assembly of the repeat subunit structure of the non-native polysaccharide on the isoprenoid lipid carrier is the transfer of glucose-P to the carrier, then any of several gene functions that carry out the same specific enzymatic reaction can be substituted. For example, in place of the gumD gene of Xanthomonas species on could substitute the spsB gene from Sphingomonas species or the pssA gene from Rhizobium species, or analogous genes from other bacteria.

The present invention further provides a method for increasing the yield of a non-native exopolysaccharide produced in a recombinant bacterial host strain by inactivating the exopolysaccharide production native to the bacterial host strain. Preferably, the inactivation is achieved by deletions or mutations in the genome of the bacterial host strain. Most preferably, the deletion or mutation inactivates the activity of a glycosyl transferase.

Most preferably, the deletion or mutation inactivates the activity of a glycosyl transferase, a polysaccharide polymerase, a secretory apparatus, or enzymes required for the synthesis of essential nucleotide-sugar precursors. For example, in Sphingomonas, inactivation of one or more of the essential substrate-specific glycosyl transferase enzymes, such as, spsB, Q, K or L, which are required for synthesis of the subunit sugar repeat structure which is attached to the carrier C55-isoprenyl phosphate eliminates synthesis of the polysaccharide produced by Sphingomonas. Likewise, mutations in a polysaccharide polymerase or in a secretion apparatus also eliminate exopolysaccharide production by a native polysaccharide producer. Production of the native polysaccharide can also be eliminated by mutations which inactivate enzymes that are essential for the synthesis of precursor nucleotide-sugars, such as the four enzymes required to synthesize the precursor dTDT-L-rhamnose:RhsA, RhsB, RhsC, or RhsD. The mutations or deletions which eliminate these enzyme or protein activities can either directly inactivate these enzymes by altering the structures and activities of the enzymes or indirectly inactivate the enzymes by blocking or modulating the expression of the genes that code for these enzymes or proteins.

The present invention also provides a method for minimizing contaminating cellulase activity in xanthan gum produced by fermentation by fermenting a recombinant Sphingomonas species strain transformed with genes from the genome of *X. campestris*, which are necessary for establishing the production of xanthan gum in the Sphingomonas species.

All of the embodiments use the following bacterial strains, recombinant DNA procedures, and growth media:

Strain X59 (ATCC 55298—see U.S. Pat. No. 5,194,386, col. 8–9) is a spontaneous rifampicin-resistant mutant derived from wild type *X. campestris* B1459 (Thome, L., et al., 1987, J Bacteriol 169: 3593–3600). Cloned DNA segments and site-specific chromosomal deletions are diagramed in FIG. 2. Plasmid XCc8 is a member of a cosmid library (Thorne, L, et al., 1987, J Bacteriol 169: 3593–3600) and was obtained by inserting a segment of about 24 kilobase pairs kbp) of chromosomal DNA from strain X59 into the mobilizable broad-host-range plasmid vector pRK311 (Ditta, G., et al., 1985, Plasmid 13: 149–153). The DNA segment carried by plasmid XC600(gumB-M) was derived from plasmid XCc8 by standard methods of DNA isolation, digestion with restriction endonucleases, and ligation (Maniatis, T., et al., 1982, Molecular cloning: a laboratory manual. Cold Spring Harbor Laboratory, Cold Spring Harbor). The insert in plasmid XC600 spans the NdeI-SalI segment of XCc8 corresponds to nucleotide 919-15400 of the gum sequence in GenBank accession number U22511, shown in Sec. ID No.1 hereof. (GenBank, National Center for Biotechnology Information, National Library of Medicine, Bethesda, Md. 20894, www.ncbi.nlm.gov/web/genbank). Plasmid XC 1483 includes nucleotide 3460 (BamHI) through 7959 (BamHI) (Pollock, T. J., et al., 1994, J Bacteriol 176: 6229–6237). Plasmids S88c1, and S88c3 are members of a cosmid library (Yamazaki, M, et al., 1996, J Bacteriol 178: 2676–2687) that were derived from a partial digestion with SalI enzyme of S88 chromosomal DNA, followed by ligation to the vector pRK311. The nucleotides deleted in strain S88ATn358 include 4485 (BamHI) through 24646 (EcoRI) in the S88 sequence (GenBank accession U51197 Sec. ID No. 2 hereof). Strain S88m265 is defective in spsB (Yamazaki, M., et al., 1996, J Bacteriol 178: 2676–2687).

DNA transformation into *E. coli,* tri-parental conjugal mating of broad-host-range plasmids into Sphingomonas or *X. campestris,* and selection methods were described (Yamazaki, M, et al., 1996, J Bacteriol 178: 2676–2687).

Luria-Bertani and M9 salts are standard media (Pollock, T. J., et al., 1994, J Bacteriol 176: 6229–6237). M9+YE is M9 salts supplemented with 0.05% w/v yeast extract. YM medium contains 3 g Bacto yeast extract, 3 g malt extract, 5 g Bacto peptone, and 10 g D-glucose per liter of deionized water. ¼ YM-G medium is YM diluted with 3 volumes of water and with no added glucose. The amounts of antibiotics used were as follows: rifampicin, 50 mg $L^{-1}$; streptomycin, 50 mg $L^{-1}$; kanamycin, 50 mg $L^{-1}$; and tetracycline, 6–15 mg $L^{-1}$ (Sigma Chemical Co.). Low viscosity carboxymethylcellulose (1% w/v final, Sigma Chemical Co.) was mixed with TSA blood agar base (Difco), and then cultures were spotted onto the surface of the medium and grown for 4–7 days at 30° C. Zones of hydrolysis of carboxymethylcellulose were observed by gently flooding the plate with 0.1% (w/v) Congo red dye for 30 min followed by destaining with 1M NaCl for 30 min. The diameters of the zones were then measured to compare the relative cellulase activity of the various cultures.

The following chemical and physical analyses of exopolysaccharides were used in the examples:

Extracellular xanthan gum or sphingan S-88 was precipitated from liquid culture medium with 2–3 volumes of isopropyl alcohol, and then dried at 80° C. before weighing. Hydrolysis mixtures contained 0.5–5 mg of polysaccharide and 130–260 μM (v/v) trifluoroacetic acid in high performance liquid chromatography (HPLC) water, and were incubated for 16 h at 95° C. The samples were dried under vacuum, resuspended in 100 μl HPLC water, dried again, and finally resuspended in 100 μl of HPLC water. Samples and sugar standards were separated on a CarboPac PA-1 anion-exchange column and the sugar compositions were quantitated with a Dionex DX500 HPLC system as described previously (Clarke, A. J., et al., 1991, Anal Biochem 199: 68–74). Assays for acetyl (Hestrin, S. 1949, J Biol Chem 180: 249–261) and pyruvyl (Duckworth, M, et al., 1970, Chem Ind 23: 747–748) groups have been described.

Samples of polysaccharides (10 mg, powdered) were dissolved in 2 ml deionized water at 80° C. for 60 min in glass test tubes with an equal weight of locust bean gum and bromphenol blue dye (100 μg $ml^{-1}$). After cooling for 2 h the tubes were rotated to horizontal for photography. Failure to gel resulted in horizontal movement of the mixed slurry.

A sample of commercial xanthan gum (Keltrol, Kelco Company) was used for physical and chemical comparisons.

For xanthan-guar mixtures each polysaccharide was dissolved in 100 mM KCl at 0.1% w/v, and solution viscosities were measured at 20–25 ° C. at several rpm with a Brookfield LVTDV-II viscometer and spindle 18.

DEPOSITS

The following deposits have been made in connection with the present invention:

1. *Sphingomonas paucimobilis* (ATCC 29837) containing plasmid XCc8 ATCC Designation No. 98479;

2. Sphingomonas strain S88ATn358 containing plasmid XCc8 ATCC Designation 98480.

The above deposits were made with the American Type Culture Collection located at 10801 University Blvd., Manassas, Va. 20110-2209m pursuant to the Budapest Treaty for the International Recognition of the Deposit of Microorganisms for the Purposed of Patent Procedure. All restrictions on the availability of the materials deposited will be irrevocably removed upon the issuance of a patent thereon.

All other microorganisms and/or DNA segments, plasmids, and the like referred to herein are publicly available from the American Type culture collection in Manassas, Va.

EXAMPLE 1

Inter-generic expression of genes coding for polysaccharide biosynthesis

Referring to FIG. 2, maps of *X. campestris* gum and Sphingomonas S88 sps genes, boundaries of specific segments cloned in plasmids, and deletions in bacterial chromosomes are shown. The arrows above the genes indicate the direction of transcription. The horizontal lines indicate the extent of the cloned DNA included in each plasmid with the included genes within parentheses. The dashed lines indicate the regions deleted from mutant chromosomes . The gumB through M genes (GenBank accession U22511) span about 14 kbp and the spsG through urf34 genes (GenBank accession U51197) include about 29 kbp.

The original cosmid clones and specific subcloned segments (diagramed in FIG. 2) were transferred by conjugal mating into *X. campestris* and Sphingomonas recipients. The type of EPS secreted into the medium was determined from the appearance of colonies and liquid cultures, and from the physical properties and carbohydrate compositions of the recovered polysaccharides.

As described in Table 1 and the legend, X. campestris X59 (Gum+), Sphingomonas S88 (Sps+) and the polysaccharide-negative mutant S88m265 (Sps−), have readily distinguished colony morphologies and characteristics in liquid culture. From a visual inspection, one can not only determine if any EPS is being secreted, but also whether the EPS is sphingan S-88 or xanthan gum. EPS samples were acid hydrolyzed, and the identity and amounts of monosaccharide(s) were determined. The xanthan gum secreted from X. campestris contained two neutral sugars, with glucose representing about 67% and mannose about 33% of the sum of the peak areas for the neutral sugars on the HPLC chromatograms. By contrast, sphingan S-88 contained about 18% rhamnose, 59% glucose, and 23% mannose. The sugar components distinguished xanthan gum from sphingan S-88.

The colonial appearance (Sps+) and composition of neutral sugars from the polysaccharides secreted by the recipient S88m265 carrying plasmid S88c1 indicated that the plasmid, which carries a normal spsB gene, restored sphingan S-88 synthesis to the mutant. Plasmid XC1483 with the X. campestris gumD gene also restored sphingan S-88 synthesis to S88m265.

Of particular interest is that a mixture of neutral sugars composed of about one-fourth sphingan S-88 and three-fourths xanthan gum was obtained when plasmid XCc8, which carries gum genes, was introduced into S88m265. This recombinant strain has all of the genes needed to make both exopolysaccharides in strain S-88. Thus, with the present invention, it is possible to obtain two different exopolysaccharides from the same organism at the same time.

TABLE 1

Sugar compositions of bacterial exopolysaccharides

| Donor plasmids | Bacterial recipient and phenotype | Recombinant phenotype[a] | Percent of total neutral sugars | | |
|---|---|---|---|---|---|
| | | | Rha | Glc | Man |
| — | X. campestries X59 Gum+ | | 0 | 67 | 33 |
| — | Sphingomonas S88 Sps+ | | 18 | 59 | 23 |
| S88c1 | S88m265 (SpsB−) | Sps+ | 19 | 62 | 19 |
| XC1483 | " | Sps+ | 22 | 61 | 17 |
| XCc8 | " | Sps/Gum+ | 7 | 64 | 29 |
| S88c3 | S88ΔTn358 (Sps−) | Sps+ | 19 | 63 | 19 |
| XCc8 | " | Gum+ | 0 | 64 | 36 |
| XC600 | " | Gum+ | 0 | 62 | 37 |
| XC566 | S88ΔTm372 (Sps−) | Gum− | | | |
| XCc8 | S88m134 (SpsB− RhsD−) | Gum+ | | | |
| XCc8 | S. paucimobilis ATCC 29837 | Gum+ | | | |

[a]Gum+ indicates a wild-type X. campestris-like appearance caused by the secretion of viscous xanthan gum, with large (3–5 mm in four days at 30° C.), shiny, mucoid, light-yellow-colored colonies on solid YM medium and a viscous culture broth in liquid YM medium with non-aggregated cells.
Sps+ indicates a wild-type appearance typical of Sphingomonas strains secreting a capsular sphingan polymer: colonies are opaque to transmitted light, shiny but not viscous, and produce viscous liquid culture broths containing aggregates of cells.

By deleting certain sps genes from the S88 chromosome we obtained synthesis in Sphingomonas of xanthan gum alone. Although plasmid S88c3 (sps genes) restored synthesis of sphingan S-88 to the deletion mutant S88ΔTn358, plasmids XCc8 and XC600 (gum genes) caused the synthesis of a polysaccharide that matched the neutral sugar percentages of xanthan, and lacked rhamnose.

Plasmid XCc8 caused the synthesis of only xanthan gum in a double mutant of Sphingomonas (S88m134) which has defects in glucosyl-IP transferase (SpsB−) and in synthesis of the essential dTDP-rhamnose substrate (RfbD−). We also observed xanthan gum synthesis in the type strain for the S. paucimobilis genus, ATCC 29837, which otherwise does not secrete any polysaccharide. Physical studies on this polysaccharide detailed in Example 3 confirmed that it was xanthan gum.

EXAMPLE 2

Detection of gene function in recombinants

In order to determine if the acetylase (gumF and G) and pyruvylase (gumL) genes of X. campestris were functioning in Sphingomonas we measured the amounts of each component for samples of the recombinant and commercial xanthan gums. The degree of acetylation for the recombinant sample (S88ΔTn358 with plasmid XCc8) exceeded that for the commercial xanthan gum by a few percent and was similar to the degree of acetylation for xanthan gum made by X. campestris X59 while growing under the same conditions as the recombinant Sphingomonas. The recombinant samples were 4–6% by weight as pyruvate compared to 5–6% for commercial xanthan (Keltrol) and xanthan made by X. campestris X59.

EXAMPLE 3

Physical analyses of recombinant xanthan gum

Three physical properties of recombinant and commercial xanthan gum were compared. First, the viscosity synergism expected for mixtures of xanthan and guar gums was observed for the recombinant samples (Table 2). Solution viscosities were measured for samples with and without added guar gum. The viscosities of the mixtures of guar gum with either commercial xanthan gum or the recombinant samples were higher than the sum of the viscosities of the unmixed polysaccharides. Second, xanthan gum is unique in forming a rigid gel in the presence of locust bean gum. Rigid gels were formed by mixing locust bean gum with commercial xanthan gum or with any one of three recombinant samples: plasmid XCc8 in either S88m265, S88ΔTn358, or S. paucimobilis ATCC 29837. Third, the viscosity of each recombinant xanthan sample was shear thinning like commercial xanthan gum. These three physical tests confirmed that the EPS secreted by the recombinant Sphingomonas strains was comparable to xanthan gum.

TABLE 2

Viscosity synergism for mixtures of exopolysaccharides and guar gum

| | Viscosity (cp)[a] | |
|---|---|---|
| EPS | EPS alone | EPS with guar |
| None | — | 4 |
| xanthan gum | 22 | 49 |
| X59 | 27 | 63 |
| S88m265/XCc8 | 7 | 18 |
| S88ΔTn358/XCc8 | 9 | 27 |
| ATCC29837/XCc8 | 7 | 29 |

[a]Centipoise (cp) for spindle 18 at 12 rmp for final concentrations of each polymer at 0.1% in 100 mM KCl at room temperature

EXAMPLE 4

Alternative culture conditions

The results in Table 3 indicate that the recombinant Sphingomonas strains, in contrast to *X. campestris*, converted either lactose or glucose to xanthan gum to a similar extent.

TABLE 3

Cell densities and xanthan gum yields for shake flask cultures.

| Growth medium, temperature, and sugar substrate | X59 A600 | X59 mg | S88ΔTn358 with XCc8 A600 | S88ΔTn358 with XCc8 mg | ATCC 29837 with XCc8 A600 | ATCC 29837 with XCc8 mg |
|---|---|---|---|---|---|---|
| 1/4 YM-G |  |  |  |  |  |  |
| 30° C. glucose | 1.1 | 43 | 6.0 | 62 | 2.9 | 37 |
| 33° C. glucose | 0.8 | 34 | 4.8 | 49 | 2.6 | 33 |
| 30° C. lactose | 0.4 | 16 | 5.4 | 67 | 3.4 | 39 |
| M9+YE |  |  |  |  |  |  |
| 30° C. glucose | 2.4 | 84 | 2.1 | 30 | 4.9 | 55 |
| 30° C. lactose | 0.2 | 9 | 2.3 | 30 | 6.3 | 53 |

1/4 YM-G and M9+YE were supplemented with either glucose or lactose to 2% w/v. Culture density was measured as the absorbance at 600 nm. The yield of xanthan gum (mg) is the average for samples of 10 ml taken from two separately inoculated flasks after 48 h (1/4YM-G) or 42 h (M9+YE). The cultures were centrifuged to remove cells before precipitation of the polysaccharides with alcohol.

Production rates and yields for large scale xanthan gum fermentations are sensitive to temperature and aeration. The highly viscous broth requires considerable stirring and cooling to achieve maximum productivity. Although *X. campestris* produces xanthan gum optimally at about 28° C., Sphingomonas strains are known to grow at temperatures up to about 37° C.

As shown in Table 3, the recombinant Sphingomonas strains grew at 30° C. and 33° C. In the case of recombinant ATCC 29833 with XcC8, the yields of gum were about equivalent to the native gum producer X-59 at both 30° C. and 33° C. in 1/4YM-G media. However, the case of the recombinant S88ΔTn358 with XCc8 in 1/4YM-G media, the yields of gum were significantly above those of the native gum producer X59 at both temperatures.

This is an important aspect of the present invention since, as the fermentation is exothermic, a major energy requirement is cooling of the fermentation broth. With the present invention, the fermentation can be carried out at a higher temperature, in the range from about 30 to 33 ° C. This means that less cooling is required and a substantial energy cost savings can be realized with the present invention as compared with the conventional fermentation conditions used for xanthan gum production.

EXAMPLE 5

Reduction of cellulase contamination in xanthan gum

The presence of contaminating cellulase in xanthan gum is disadvantageous in commercial applications where xanthan is mixed with or contacts cellulosic polymers. As judged by measuring the zones of hydrolysis surrounding cultures spotted onto agar plates containing carboxymethylcellulose, we found that the inventive Sphingomonas recombinants showed less than one-eighth of the cellulase activity observed for *X. campestris* strain X59. This means that xanthan gum as produced from the inventive strains contains significantly decreased amounts of contaminating cellulase as compared with xanthan gum obtained from X59. As used herein, "as produced" means the xanthan product as obtained directly from the broth without any steps, after-treatments or procedures taken to remove cellulase therefrom. Accordingly, the as produced xanthan gum obtained with the present invention is advantageous since it avoids the increased costs and steps normally required with conventional xanthan product to remove or decrease the cellulase content.

EXAMPLE 6

Prophetic Example To Show How to Construct and Use Subsets of the Larger Segment Construction and use of foreign genetic material from the genome of Xanthomonas lacking the acetylase (gumF and gumG), pyruvylase (gumL), or glycosyl transferase (gumD) genes.

Three segments of DNA containing the gumBCDE, gumHIJK, and gumM genes can be isolated from the recominant plasmid carrying the XC6000 portion of the Xanthomonas genome. Similarly, two segments containing the gumBC and gumEFGHIJKLM genes can be isolated. The genes can be prepared by cleavage of the XC600 segment with specific restriction endonucleases or by amplification using the polymerase chain reaction, and then purified by electrophoresis through an agarose gel. When the polymerase chain reaction is used the primer segments will contain specific sequences for restriction endonucleases. The three segments will be assembled by DNA ligation as a contiguous set of genes as in a genetic operon and inserted by DNA ligation into a plasmid vector that can be introduced into Sphingomonas. The DNA sequence of the gum region (Genbank number U22511, seq. ID No. 1) provides the positions of the individual gum genes, the available restriction endonuclease sites, and the sequences required to synthesize specific primers for polymerase chain reaction. All of the above-described recombinant DNA methods are routine for one of average skill in this art. The plasmid can be one of several broad host range mobilizable vectors, such as pRK311. Alternatively, the foreign genes can be inserted into the Sphingomonas chromosome by using a vector plasmid which cannot replicate autonomously with Sphingomonas. Alternative DNA sequences can be inserted into the assembled segment to modify or stimulate gene expression, such as, gene regulation sequences, promoter sequences for RNA polymerase, or ribosome binding sequences. By using modifications of these methods, one can assemble different segments lacking any one of or a combination of the gumF, gumG, gumL, or gumD genes, and thereby produce xanthan gum lacking acetyl and/or pyruvyl side groups, or lacking the glycosyl transferase GumD, where a foreign glycosyl transferase gene substitutes for the GumD function.

Alternatively, one can inactivate any one of or any combination of the gumF, gumG, gumL or gumD genes by site-specific mutagenesis to alter the specific amino acid sequence fo the proteins. Available methods for this mutagenesis include chemical changes to the DNA sequence or insertions of foreign DNA such as insertion sequences or transposons.

It is to be understood that the foregoing examples are exemplary and explanatory only and are not restrictive of the invention. Various changes may be made to the embodiments described above by one of skill in the art without departing from the scope of the invention, as defined by the following claims.

We claim:

1. A method for making a recombinant xanthan producing Sphingomonas species strain, comprising transferring a portion of the genome of *Xanthomonas campestris* into a Sphingomonas species, the genome portion comprising a set of genes selected from the group consisting of the gumB, gumC, gumD, gumE, gumF, gumG, gumH, gumI, gumJ, gumK, gumL and gumM genes of the *X. campestris* genome, wherein the transfer of the set of genes enables xanthan production in the Sphingomonas species.

2. The method of claim 1 wherein the set of genes excludes at least one gene of the group consisting of gumD, gumE, gumG and gumL.

3. A recombinant xanthan producing Sphingomonas species produced by the method of claim 2.

4. The method of claim 2 wherein the genome portion is on a plasmid.

5. A recombinant xanthan producing Sphingomonas species produced by the method of claim 4.

6. The method of claim 2 wherein the genome portion is integrated into the Sphingomonas species' genome.

7. A recombinant xanthan producing Sphingomonas species produced by the method of claim 6.

8. The method of claim 2, further comprising inactivation of native sphingan production in the Sphingomonas strain by deletion or mutation of one or more of the Sphingomonas strain's sps genes.

9. A recombinant xanthan producing Sphingomonas species produced by the method of claim 8.

10. A method of producing xanthan gum from lactose, comprising incubating a recombinant Sphingomonas species strain in a media containing lactose and harvesting the xanthan gum from the media, wherein the recombinant Sphingomonas species strain is made by the method of claim 1.

11. A xanthan gum produced by the method of claim 10.

12. The method of claim 10 wherein the lactose of the media is provided as a whey waste byproduct of cheese production.

13. A xanthan gum produced by the method of claim 12.

14. A method of producing xanthan gum from lactose, comprising incubating a recombinant Sphingomonas species strain in a media containing lactose and harvesting the xanthan gum from the media, wherein the recombinant Sphingomonas species strain is made by the method of claim 2.

15. A xanthan gum produced by the method of claim 14.

16. The method of claim 14 wherein the lactose of the media is provided as a whey waste byproduct of cheese production.

17. A xanthan gum produced by the method of claim 16.

18. A method of producing xanthan gum from lactose, comprising incubating a recombinant Sphingomonas species strain in a media containing lactose and harvesting the xanthan gum from the media, wherein the recombinant Sphingomonas species strain is made by the method of claim 8.

19. A xanthan gum produced by the method of claim 18.

20. The method of claim 18 wherein the lactose of the media is provided as a whey waste byproduct of cheese production.

21. A xanthan gum produced by the method of claim 20.

* * * * *